(12) United States Patent
Amlot et al.

(10) Patent No.: US 6,383,487 B1
(45) Date of Patent: May 7, 2002

(54) METHODS OF TREATMENT USING CD25 BINDING MOLECULES

(75) Inventors: Peter Lloyd Amlot, London; Arne Nalpon Akbar, Richmond, both of (GB); Günther Heinrich, Riehen; Salvatore Cammisuli, Reinach, both of (CH)

(73) Assignees: Novartis AG, Basel (CH); University College London, London (GB)

( * ) Notice: Subject to any disclaimer, the term of this patent is extended or adjusted under 35 U.S.C. 154(b) by 0 days.

(21) Appl. No.: 08/479,089

(22) Filed: Jun. 6, 1995

Related U.S. Application Data

(63) Continuation of application No. 07/669,545, filed on Mar. 14, 1991.

(30) Foreign Application Priority Data

Mar. 16, 1990 (GB) .............................................. 9005962
Sep. 5, 1990 (GB) .............................................. 9019323

(51) Int. Cl.[7] ...................... A61K 39/395; C07K 16/28; C07K 16/30
(52) U.S. Cl. ................................ 424/181.1; 424/130.1; 424/133.1; 424/135.1; 424/141.1; 424/143.1; 424/144.1; 424/153.1; 424/173.1; 424/178.1; 424/183.1; 424/1.49; 530/387.1; 530/387.3; 530/388.1; 530/388.2; 530/388.22; 530/388.7; 530/388.73; 530/388.75; 530/391.1; 530/391.3; 530/391.7
(58) Field of Search .............................. 536/23.53, 23.1, 536/23.4, 23.5; 530/387.3, 388.22, 387.1, 388.1, 388.2, 388.7, 388.73, 388.75, 391.1, 391.3, 391.7; 435/240.27, 320.1, 69.1, 69.6, 440, 455, 252.3, 325, 328, 332, 334, 343, 343.1, 343.2; 424/133.1, 144.1, 130.1, 135.1, 141.1, 143.1, 153.1, 154.1, 173.1, 1.49, 178.1, 181.1, 183.1

(56) References Cited

U.S. PATENT DOCUMENTS

| | | | |
|---|---|---|---|
| 5,084,391 A | * | 1/1992 | Wijdenes et al. |
| 5,530,101 A | | 6/1996 | Queen et al. |
| 5,631,349 A | | 5/1997 | Diamantstein et al. |
| 6,013,256 A | | 1/2000 | Light et al. |

FOREIGN PATENT DOCUMENTS

| | | | |
|---|---|---|---|
| EP | 0235805 | * | 9/1987 |
| EP | 0319333 | * | 6/1989 |
| WO | 8909622 | * | 10/1989 |
| WO | WO 90/07861 | | 7/1990 |

OTHER PUBLICATIONS

Dillman J Clin Oncol. 12: 1497–1515 (1994).*
Harris et al. Tibtech 11:42–44, 1993.*
Dillman, J. Clin Oncol. 12:1497–1515, 1994.*
Fahey et al. Clin exp. Immunol. 88:1–5, 1992.*
Wijdenes et al. "Cellular Basis of ImmunoRegulation" Alan R Liss Inc. pp 551–555, 1989.*
Junghans et al. Cancer Res. 50: 1495–1502 Mar. 1990.*
Queen et al. PNAS USA 80:10029–33 1989.*
Mol. Cell Biol. 8(3):1247–52, Mar. 1988.*
J. Cell Biol. 111:2129–37, Nov. 1990.*
Science 237:1570, 1987.*
Cell 50:667, Aug. 1987.*
Bioworld Financial Watch 3(29):1–11, Apr. 1995.*
Akbar A. et al., Transplantation, vol. 50, No. 5, pp. 823–829 (1990).
Heinrich G. et al., The Journal of Immunology, vol. 143, No. 11, pp. 3589–3597 (1989).
Engert et al., "Immunotoxins Constructed With Anti–CD25 Monoclonal Antibodies and Deglycosylated Ricin A–Chain Have Potent Anti–Tumour Effects Against Human Hodgkin Cells In Vitro and Solid Hodgkin Tumours in Mice." *Int. J. Cancer.* 49, 1991, pp 450–456. (1991).
Ramos et al., "Differential IL–2 Receptor Expression in Renal Allograft Recipients Treated With An Anti–IL–2–Receptor Antibody." 1989, *Transplantation*, vol. 48, pp 415–420.
Nashan et al., *The Lancet*, vol. 350, pp. 1193–1198 (1997).
Simulect® Package Insert, Novartis Pharmaceuticals Corporation, May 12, 1998.

* cited by examiner

*Primary Examiner*—Phillip Gambel
(74) *Attorney, Agent, or Firm*—Diane E. Furman

(57) ABSTRACT

Novel monoclonal antibodies to the CD25 antigen are characterized by the amino acid sequence of their hypervariable regions. Initially produced in murine form, they may be converted to chimeric or humanized forms, immunoconjugates or antibody fragments (generally described as binding molecules). The products are useful for the prophylaxis or treatment of transplant rejection, paticularly in combination with other antibodies to activated T-cells, for example CD7 antibodies.

29 Claims, 11 Drawing Sheets

METHODS OF TREATMENT USING CD25 BINDING MOLECULES

This is a continuation of application Ser. No. 07/669,545, filed Mar. 14, 1991.

This invention relates to immunosuppression and more particularly provides monoclonal antibodies and other binding molecules against the CD25 antigen.

In organ transplant surgery, particularly kidney, liver, heart, lung and bone marrow transplant surgery, it is necessary to suppress the immune system of the graft recipient to minimise the likelihood of graft rejection after surgery. Various immunosuppressive drugs have been proposed for this purpose but their use has to be carefully controlled since, in addition to undesirable side-effects arising from the use of certain immunosuppressive agents, there is also the difficulty that the immunosuppressive action makes the graft recipient particularly susceptible to infection by bacteria and viruses that would be controlled by a normal immune system. Immunosuppressive agents that have been used successfully in clinical practice include steroids, azathioprine and cyclosporin A. It is necessary in clinical practice to attempt to balance the degree of immunosuppression necessary to prevent or treat graft rejection episodes with the retention of a certain amount of the recipient's immune system to combat other infectious agents and, at the same time, to keep any possible undesirable side-effects under control.

In addition to the use of immunosuppressive drugs, attention has also focused upon the use of certain monoclonal antibodies (MAbs) to suppress immune reactions, in particular, attention has been paid to monoclonal antibodies that recognise various surface antigens of T-cells. Here too, problems have been encountered in clinical practice, namely that prior art antibodies were either too powerful or not sufficiently effective, and sometimes caused severe side effects such as high fever.

These MAb's are generally designated by a CD (Cluster Determination) number assigned by successive Leucocyte Typing Workshops. Although a term such as CD3 is now frequently applied to the cell surface antigen, and a MAb to this antigen is often described as "anti-CD3", in the following description terms such as CD3, CD25 etc. will be applied to MAb's and the corresponding cell surface antigens will be described as "CD3 antigen" etc.

In particular, monoclonal antibodies to membrane antigens present on all T-cells (also called pan T-cell antigens) such as the CD3 antigen are very potent antibodies in that they have an overall suppressive activity on the immune system. Therefore, the human body may be deprived of the immediate immune response usually mediated by the memory T-cells once an infection occurs. This is certainly not desirable when attempting to prevent rather than to cure graft rejection episodes. A treatment suitable for use in prophylaxis should be essentially selective, i.e. the pool of memory T-cells should be kept intact while the category of T-cells (activated T-cells) which could be directly involved in a rejection event should be inactivated.

This desirable goal may be achieved using antibodies to activated T-cells. These T-cells are characterised by the presence of the high affinity IL-2 receptor on their membrane surface. The high affinity IL-2 receptor is composed of at least two different polypeptide chains, an α-chain also known as the CD25 antigen, and a β-chain. Resting T-cells do not express this high affinity receptor but low and intermediate affinity receptors which consist of α- or β-chain homodimers. A CD25 antibody which interferes with the binding of IL-2 to its high affinity receptor and therefore selectively suppresses the immune response, is an antibody of choice for the prophylaxis of graft rejection episodes.

Natural immunoglobulins or antibodies comprise a generally Y-shaped multimeric molecule having an antigen-binding site at the end of each upper arm. The remainder of the structure, in particular the stem of the Y mediates effector functions associated with the immunoglobulins. The general structure of an antibody of the IgG class is shown schematically in FIG. 1A. Both heavy and light chains comprise a variable domain and a constant part. An antigen binding site consists of the variable domain of a heavy chain associated with the variable domain of a light chain. The variable domains of the heavy and light chains have the same general structure which is illustrated in FIG. 1B.

More particularly, the antigen binding characteristics of an antibody are essentially determined by 3 specific regions in the variable domain of the heavy and light chains which are called hypervariable regions or complementarity determining regions (CDRs). As shown in FIG. 1B, these 3 hypervariable regions alternate with 4 framework regions, (FRs) whose sequences are relatively conserved and which are not directly involved in binding. The CDRs form loops and are held in close proximity by the framework regions which largely adopt a β-sheet conformation. The CDRs of a heavy chain together with the CDRs of the associated light chain essentially constitute the antigen binding site of the antibody molecule.

The determination as to what constitutes an FR or a CDR region is usually made by comparing the amino acid sequence of a number of antibodies raised in the same species. The general rules for identifying the CDR and FR regions are given in Table C.

Furthermore, it has been recently found that the contribution made by a light chain variable domain to the energetics of binding is small compared to that made by the associated heavy chain variable domain and that isolated heavy chain variable domains have an antigen binding activity on their own. Such molecules are now commonly referred to as single domain antibodies.

Several murine CD25 MAbs already exist and include 33B3-1 (Immunotech-Merieux), BDαIL-2R (Becton-Dickinson), 2C8 (Amersham), Campath 6 (MRC, Cambridge) and ATH207 (free University, Berlin). However, it has now been found that a novel mouse CD25 antibody of the IgG2a isotype, hereinafter called RFT5-IgG2a, has better properties than the CD25 antibodies of the prior art especially with regard to binding affinity, and that it is possible to construct other CD25 binding molecules having the same hypervariable regions as RFT5-IgG2a.

Accordingly, the invention provides a CD25 binding molecule which comprises at least one antigen binding site comprising at least one domain which comprises in sequence, the hypervariable regions CDR1, CDR2 and CDR3; said CDR1 having the amino acid sequence Arg-Tyr-Trp-Met-His (SEQ. ID. NO: 7), said CDR2 having the amino acid sequence Ala-Ile-Tyr-Pro-Gly-Asn-Ser-Asp-Thr-Ser-Tyr-Asn-Gln-Lys-Phe-Glu-Gly (SEQ. ID. NO: 8), and said CDR3 having the amino acid sequence Asp-Tyr-Gly-Tyr-Tyr-Phe-Asp-Phe (SEQ. ID. NO: 9); and direct equivalents thereof.

In a first aspect of the invention, the CD25 binding molecule comprises a single antigen binding site comprising a single domain.

In a second aspect of the invention, the CD25 binding molecule comprises at least one antigen binding site comprising:

a) a first domain comprising in sequence the hypervariable regions CDR1, CDR2 and CDR3; said CDR1 having the amino acid sequence Arg-Tyr-Trp-Met-His (SEQ. ID. NO: 7), said CDR2 having the amino acid sequence Ala-Ile-Tyr-Pro-Gly-Asn-Ser-Asp-Thr-Ser-Tyr-Asn-Gln-Lys-Phe-Glu-Gly (SEQ. ID. NO: 8), and said CDR3 having the amino acid sequence Asp-Tyr-Gly-Tyr-Tyr-Phe-Asp-Phe (SEQ. ID. NO: 9) and, b) a second domain comprising in sequence the hypervariable regions CDR1', CDR2' and CDR3', said CDR1' having the amino acid sequence Ser-Ala-Ser-Ser-Ser-Ile-Ser-Tyr-Met-Gln (SEQ. ID. NO: 10), said CDR2' having the amino acid sequence Asp-Thr-Ser-Lys-Leu-Ala-Ser (SEQ. ID. NO: 11), and said CDR3' having the amino acid sequence His-Gln-Arg-Ser-Ser-Tyr-Thr (SEQ. ID. NO: 12);

and direct equivalents thereof.

Unless otherwise indicated, any polypeptide chain is hereinafter described as having an amino acid sequence starting at the N-terminal extremity and ending at the C-terminal extremity.

When the antigen binding site comprises both the first and second domains, these may be located on the same polypeptide molecule or, preferably, each domain may be on a different chain, the first domain being part of an immunoglobulin heavy chain or fragment thereof and the second domain being part of an immunoglobulin light chain or fragment thereof.

By "CD25 binding molecule" is meant any molecule capable of binding to the CD25 antigen either alone or associated with other molecules to form high affinity IL-2 receptors. The binding reaction may be shown by standard methods (qualitative assays) including, for example, a bioassay for determining the inhibition of IL-2 binding to its receptor or any kind of binding assays, with reference to a negative control test in which an antibody of unrelated specificity, e.g. an anti-lysosyme antibody, is used. Advantageously, the binding of the molecule of the invention to the CD25 antigen may be shown in a competitive binding assay using the AHT207, BDαIL-2-R or 33B3-1 antibody as competitors. Preferably, the AHT207 or BDαIL-2-R antibody will be chosen as competitors. A particular example of a binding assay is given below.

Human peripheral blood mononuclear cells (HPBM) are grown in culture medium RPMI 1640 supplemented with 2 mM L-glutamine, 100 units/ml penicillin, 100 µg/ml streptomycin, 25 mM sodium bicarbonate and 10% fetal calf serum (FCS). 1 µg/ml phytohemagglutinin (PHA) is used to stimulate HPBM. After 3 days, the blasts are resuspended at a concentration of $3.10^6$/ml in phosphate buffered saline supplemented with 2% bovine serum albumin (BSA) and 2% azide. 50 µl samples of this suspension are incubated for 10 mn, at 20° C., under non-capping conditions, with graded concentrations of a blocking antibody (competitor) from 1 to 100 µg/ml. Then 1 µg/ml of biotinylated antibody of the invention is added to the cells and the incubation is continued for 10 min. Cells are washed and further incubated for 10 min with fluorescein-labelled streptavidin. Cells are again washed, fixed with formalin and analysed with a fluoro-cytometer which detects the binding of the biotinylated antibody. In parallel, an experiment is carried out with a biotinylated antibody of an unrelated specificity, as a negative control.

Examples of antigen binding molecules include antibodies as produced by B-cells or hybridomas and chimeric or humanized antibodies or any fragment thereof, e.g. F(ab')$_2$ and Fab fragments, as well as single chain or single domain antibodies.

A single chain antibody consists of the variable domains of an antibody heavy and light chains covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin. By "humanized antibody" is meant an antibody in which the hypervariable regions (CDRs) are of non-human (e.g. murine) origin, while all or substantially all the other parts of the immunoglobulin e.g. the constant regions and the highly conserved parts of the variable domains, i.e. the framework regions, are of human origin. A humanized antibody may however retain a few amino acids of the murine sequence in the parts of the framework regions adjacent to the hypervariable regions.

Hypervariable regions may be associated with any kind of framework regions, preferably of murine or human origin. Suitable framework regions are described in "Sequences of proteins of immunological interest", Kabat E. A. et al, US department of health and human services, Public health service, National Institute of Health. However, the preferred heavy chain framework is that of RFT5-IgG2a, which is shown in Table A and Seq. Id. Nos: 1 to 3. It consists in sequence of FR1, FR2, FR3 and FR4 regions. In a similar manner, Table B and Seq. Id. Nos. 4 to 6 shows the preferred RFT5-IgG2a light chain framework which consists, in sequence, of FR1', FR2', FR3' and FR4' regions.

Accordingly, the invention also provides a CD25 binding molecule which comprises at least one antigen binding site comprising either a first domain having an amino acid sequence substantially identical to that shown in Seq. Id. No. 1 starting with the amino acid at position 1 and ending with the amino acid at position 117 or a first domain as described above and a second domain having an amino acid sequence substantially identical to that shown in Seq. Id. No. 4, starting with amino acid at position 1 and ending with the amino acid at position 104.

Monoclonal antibodies raised against a protein naturally found in all humans must necessarily be developed in a non-human system e.g. in mice. As a direct consequence of this, a xenogenic antibody as produced by a hybridoma, when administered to humans, elicits an undesirable immune response which is predominantly mediated by the constant part of the xenogenic immunoglobulin. This clearly limits the use of such antibodies as they cannot be administered over a prolonged period of time. Therefore it is particularly preferred to use single chain, single domain, chimeric or humanized antibodies which are not likely to elicit a substantial allogenic response when administered to humans.

In view of the foregoing, a more preferred CD25 binding molecule of the invention is selected from a chimeric anti-CD25 antibody which comprises at least a) one immunoglobulin heavy chain or fragment thereof which comprises (i) a variable domain comprising in sequence the hypervariable regions CDR1, CDR2 and CDR3 and (ii) the constant part or fragment thereof of a human heavy chain; said CDR1 having the amino acid sequence Arg-Tyr-Trp-Met-His (SEQ. ID. NO: 7), said CDR2 having the amino acid sequence Ala-Ile-Tyr-Pro-Gly-Asn-Ser-Asp-Thr-Ser-Tyr-Asn-Gln-Lys-Phe-Glu-Gly (SEQ. ID. NO: 8), and said CDR3 having the amino acid sequence Asp-Tyr-Gly-Tyr-Tyr-Phe-Asp-Phe (SEQ. ID. NO: 9) and b) one immunoglobulin light chain or fragment thereof which comprises (i) a variable domain comprising in sequence the hypervariable regions CDR1', CDR2' and CDR3' and (ii) the constant part or fragment thereof of a human light chain; said CDR1' having the amino acid sequence Ser-Ala-Ser-Ser-Ser-Ile-Ser-Tyr-Met-Gln (SEQ. ID. NO: 10), said CDR2' having the amino acid sequence Asp-Thr-Ser-Lys-Leu-Ala-Ser (SEQ. ID. NO: 11), and said CDR3' having the amino acid sequence His-Gln-Arg-Ser-Ser-Tyr-Thr (SEQ. ID. NO: 12);

and direct equivalents thereof.

Alternatively, a CD25 binding molecule of the invention may be selected from a single chain binding molecule which comprises an antigen binding site comprising a) a first domain comprising in sequence the hypervariable regions CDR1, CDR2 and CDR3, said hypervariable regions having the amino acid sequences as shown in Table A and Seq. Id. Nos. 1 to 3, b) A second domain comprising in sequence the hypervariable regions CDR1', CDR2' and CDR3', said hypervariable regions having the amino acid sequences as shown in Table B and Seq. Id. Nos. 4 to 6 and c) a peptide linker which is bound either to the N-terminal extremity of the first domain and to the C-terminal extremity of the second domain or to the C-terminal extremity of the first domain and to the N-terminal extremity of second domain;

and direct equivalents thereof.

As it is well known, minor changes in an amino acid sequence such as deletion, addition or substitution of one or several amino acids may lead to an allelic form of the original protein which has substantially identical properties. Thus, by the term "direct equivalents thereof" is meant either any single domain CD25 binding molecule (molecule X)

(i) in which the hypervariable regions CDR1, CDR2 and CDR3 taken as a whole are at least 80% homologous, preferably at least 90% homologous, more preferably at least 95% homologous to the hypervariable regions as shown in Seq. Id. No. 3 and, (ii) which is capable of inhibiting the binding of IL-2 to its receptor substantially to the same extent as a reference molecule having framework regions identical to those of molecule X but having hypervariable regions CDR1, CDR2 and CDR3 identical to those shown in Seq. Id. No. 3;

or any CD25 binding molecule having at least two domains per binding site (molecule X')

(i) in which the hypervariable regions CDR1, CDR2, CDR3, CDR1', CDR2' and CDR3' taken as a whole are at least 80% homologous, preferably at least 90% homologous, more preferably at least 95% homologous to the hypervariable regions as shown in Seq. Id. Nos. 3 and 6 and (ii) which is capable of inhibiting the binding of IL-2 to its receptor substantially to the same extent as a reference molecule having framework regions and constant parts identical to molecule X' but having hypervariable regions CDR1, CDR2, CDR3, CDR1', CDR2' and CDR3' identical to those shown in Seq. Id. Nos. 3 and 6.

This last criterion may be conveniently tested in various assays including a Mixed Lymphocyte Reaction (MLR) bioassay, an antigen specific HPBM response bioassay and an IL-2 dependent T lymphoblast proliferation bioassay. Such assays are described hereinafter in the text. By the term "to the same extent" is meant that the reference and the equivalent molecules exhibit, on a statistical basis, essentially identical IL-2 binding inhibition curves in one of the bioassays referred to above.

Most preferably, the chimeric CD25 antibody comprises at least a) one heavy chain which comprises a variable domain having an amino acid sequence substantially identical to that shown in Seq. Id. No. 1 starting with glutamic acid at position 1 and ending with serine at position 117 and the constant part of a human heavy chain; and b) one light chain which comprises a variable domain having an amino acid sequence substantially identical to that shown in Seq. Id. No. 4 starting with glutamine acid at position 1 and ending with lysine acid at position 104 and the constant part of a human light chain.

The constant part of a human heavy chain may be of the $\gamma_1, \gamma_2, \gamma_3, \gamma_4, \mu, \alpha_1, \alpha_2, \delta$ or $\epsilon$ type, preferably of the $\gamma$ type, more preferably of the $\gamma_1$ type, whereas the constant part of a human light chain may be of the $\kappa$ or $\lambda$ type (which includes the $\lambda_1, \lambda_2$ and $\lambda_3$ subtypes) but is preferably of the $\kappa$ type. The amino acid sequence of all these constant parts are given in Kabat et al (Supra).

Conjugates of the CD25 binding molecules of the invention, e.g. enzyme or toxin or radioisotope conjugates, are also included within the scope of the invention.

A CD25 binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided (i) DNA molecules encoding a single domain CD25 binding molecule, of the invention, a single chain CD25 binding molecule of the invention, a heavy or light chain or fragments thereof of a CD25 binding molecule of the invention and (ii) the use of the DNA molecules of the invention for the production of a CD25 binding molecule of the invention by recombinant means.

The present state of the art is such that the skilled man will be able to synthetize the DNA molecules of the invention given the information provided herein i.e. the amino acid sequences of the hypervariable regions and the DNA sequences coding for them. A method for constructing a variable domain gene is for example described in EPA 239 400 and may be briefly summarized as follows: A gene encoding a variable domain of a MAb of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given in Seq. Id. No. 1 or 4. These cassettes are provided with sticky ends so that they can be ligated at the junctions of the framework. A protocol for achieving a DNA molecule encoding an immunoglobulin variable domain is shown in FIG. 5.

Furthermore, it is not necessary to have access to the mRNA from a producing hybridoma cell line in order to obtain a DNA construct coding for the MAbs of the invention. Thus PCT application WO 90/07861 gives full instructions for the production of a MAb by recombinant DNA techniques given only written information as to the nucleotide sequence of the gene. The method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649.

In view of the foregoing, and since the mouse MAb as naturally secreted by the hybridoma is not the preferred type of MAb, it is believed that no hybridoma deposit is necessary to comply with the criteria of sufficiency of description.

In a particular embodiment of the invention, the recombinant means for the production of a CD25 binding molecule includes first and second DNA constructs as described below:

The first DNA construct encodes a heavy chain or fragment thereof and comprises a) a first part which encodes a variable domain comprising alternatively framework and hypervariable regions, said hypervariable regions being in sequence CDR1, CDR2 and CDR3 the amino acid sequences of which are shown in Seq. Id. No. 1; this first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the heavy chain and ends with a codon encoding the last amino acid of the constant part or fragment thereof, followed by a non-sense codon.

Preferably, this first part encodes a variable domain having an amino acid sequence substantially identical to the amino acid sequence as shown in Seq. Id. No. 1 starting with the amino acid at position 1 and ending with the amino acid at position 117. More preferably the first part has the nucleotide sequence as shown in Seq. Id. No. 1 starting with the nucleotide at position 142 and ending with the nucleotide at position 492. Also preferably, the second part encodes the constant part of a human heavy chain, more preferably the constant part of the human γ1 chain. This second part may be a DNA fragment of genomic origin (comprising introns) or a cDNA fragment (without introns).

The second DNA construct encodes a light chain or fragment thereof and comprises a) a first part which encodes a variable domain comprising alternatively framework and hypervariable regions; said hypervariable regions being in sequence CDR1', CDR2' and CDR3', the amino acid sequences of which are shown in Seq. Id. No. 4; this first part starting with a codon encoding the first amino acid of the variable domain and ending with a codon encoding the last amino acid of the variable domain, and b) a second part encoding a light chain constant part or fragment thereof which starts with a codon encoding the first amino acid of the constant part of the light chain and ends with a codon encoding the last amino acid of the constant part or fragment thereof followed by a non-sense codon.

Preferably, this first part encodes a variable domain having an amino acid sequence substantially identical to the amino acid sequence as shown in Seq. Id. No. 4 starting with the amino acid at position 1 and ending with the amino acid at position 104. More preferably, the first part has the nucleotide sequence as shown in Seq. Id. No. 4 starting with the nucleotide at position 244 and ending with the nucleotide at position 555 Also preferably the second part encodes the constant part of a human light chain, more preferably the constant part of the human κ chain.

In the first and second DNA constructs, the first and second parts are preferably separated by an intron. In the intron located between the first and second part, an enhancer is preferably inserted. The presence of this genetic element which is transcribed but not translated, may be required for an efficient transcription of the second part. More preferably the first and second DNA constructs comprise the enhancer of a heavy chain gene advantageously of human origin.

The first or second DNA construct advantageously comprises a third part which is located upstream of the first part and which encodes part of a leader peptide; this third part starting with the codon encoding the first amino acid and ending with the last amino acid of the leader peptide. This peptide is required for secretion of the chains by the host organism in which they are expressed and is subsequently removed by the host organism. Preferably, the third part of the first DNA construct encodes a leader peptide having an amino acid sequence substantially identical to the amino acid sequence as shown in Table A, starting with the amino acid at position −19 and ending with the amino acid at position −1. Also preferably, the third part of the second DNA construct encodes a leader peptide having an amino acid sequence as shown in Table B, starting with the amino acid at position −22 and ending with the amino acid at position −1.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, it is particularly preferred to use the promoter of an immunoglobulin gene.

The desired antibody may be produced in a cell culture or in a transgenic animal. A suitable transgenic animal may be obtained according to standard methods which include micro injecting into eggs the first and second DNA constructs placed under suitable control sequences, transferring the so prepared eggs into appropriate pseudo-pregnant females and selecting a descendant expressing the desired antibody.

When the antibody chains have to be produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin e.g. a myeloma, hybridoma or a normal immortalized B-cell, but does not express any endogeneous antibody heavy or light chain.

It is also preferred that the host organism contains a large number of copies of the vectors per cell. If the host organism is a mammalian cell line, this desirable goal may be reached by amplifying the number of copies according to standard methods. Amplification methods usually consist of selecting for increased resistance to a drug, said resistance being encoded by the expression vector.

In another aspect of the invention, there is provided a process for producing a multi-chain CD25 binding molecule which comprises (i) culturing an organism which is transformed with first and second DNA constructs of the invention and (ii) recovering an active CD25 binding molecule from the culture.

Alternatively, the heavy and light chains may be separately recovered and reconstituted into an active binding molecule after in vitro refolding. Reconstitution methods are well-known in the art; Examples of methods are in particular provided in EPA 120 674 or in EPA 125 023.

Therefore a process may also comprise
(i) culturing a first organism which is transformed with a first DNA construct of the invention and recovering said heavy chain or fragment thereof from the culture and
(ii) culturing a second organism which is transformed with a second DNA construct of the invention and recovering said light chain or fragment thereof from the culture and
(iii) reconstituting in vitro an active CD25 binding molecule from the heavy chain or fragment thereof obtained in (i) and the light chain or fragment thereof obtained in (ii).

In a similar manner, there is also provided a process for producing a single chain or single domain CD25 binding molecule which comprises (i) culturing an organism which is transformed with a DNA construct respectively encoding a single chain or single domain CD25 binding molecule of the invention and (ii) recovering said molecule from the culture.

CD25 binding molecules of the invention exhibit very good immunomodulatory activity as shown, for example, in a mixed lymphocyte reaction (MLR) bioassay (Akbar et al, J. Immunol. 140, 2171–8). The MLR is generally considered to be the in vitro equivalent of the allogeneic transplant response which leads to rejection in vivo.

1. Inhibition of the MLR

From a HPBM preparation of a first donor are aliquoted 100 μl samples containing $10^5$ HPBM to which are added various concentrations of a molecule of the invention ranging from 0 to 300 ng/ml (including these limiting values). Then each sample is mixed with a 100 μl aliquot containing $10^5$ HLA-incompatible X-irradiated HPBM of a second donor, or T-cell depleted HPBM. The mixture is incubated for 6 days at 37° C., and 1 μCi of methyl $^3$H-thymidine ($^3$H-Tdr) in 10 μl volume is then added. After 6 hours, the cell proliferation is measured by radioactivity incorporation.

In this particular assay, the molecules of the invention show an in vitro immunomodulatory activity at concentrations of from 0.3 ng/ml as shown in FIG. 6. 50% of the cellular growth is inhibited at about 3 ng/ml.

The immunomodulatory activity of the molecules of the invention may also be estimated by measuring the inhibition of antigen-specific HPBL response or the inhibition of IL-2 dependent T-lymphoblast proliferation as follows:

2. Inhibition of Antigen-specific HPBM Response

The molecules of the invention inhibit efficiently the generation of a PPD (tuberculin) specific, HLA class II restricted T-cell response, indicating their ability to inhibit the binding of endogenously produced IL-2 to its receptor. In vivo these antigen specific responses are expected to play a crucial role in the initiation of autoimmunity and transplantation rejection.

From a preparation of HPBM are aliquoted 100 μl samples containing $10^5$ HPBM to which are added various concentrations of a molecule of the invention ranging from 0 to 300 ng/ml (including these limiting values) and tuberculin (PPD) at a final concentration of 30 μg/ml. The samples are incubated for 6 days at 37° C., and 1 μCi of methyl $^3$H-thymidine is then added in a 10 μl volume. After 6 hours of incubation, cell proliferation is measured by radioactivity incorporation.

In this particular assay, the molecules of the invention show an immunomodulatory activity of from about 10 ng/ml as shown in FIG. 7. 50% of the cellular growth is inhibited at about 50 ng/ml.

3. Inhibition of IL-2 Dependent T-lymphoblast Proliferation

The molecules of the invention inhibit efficiently the IL-2 dependent growth of human T cell blasts induced by MLR or PPD stimulation. These cells are expected to play a major role in the chronicity of autoimmunity and rejection episodes.

Triplicate cultures containing $20 \times 10^3$ 5 day old PPD or MLR stimulated HPBM in a final volume of 200 μl are incubated at 37° C. for 48 hours in the presence of 5, 10 or 20 ng/ml recombinant IL-2 and a molecule of the invention at various concentrations ranging from 0 to 10 μg/ml (including these limiting values). Then $^3$H-Tdr is added. After 6 hours, cell proliferation is measured by radioactivity incorporation. In this particular assay, the molecules of the invention show an immunomodulatory activity at concentrations of from 0.1 μg/ml as shown in FIGS. 8A and 8B, 8C and 8D.

Therefore the invention also provides
(i) the use of a CD25 binding molecule of the invention in immunosuppression of a human immune system
(ii) a method of immunosuppressing the human immune system which comprises administering an immunosuppressive effective amount of a CD25 binding molecule of the invention to a patient in need of such treatment.
(iii) a pharmaceutical composition for immunosuppressing the human immune system which comprises a CD25 binding molecule of the invention and a pharmaceutically acceptable carrier or diluent.

In particular, a CD25 binding molecule of the invention is useful for preventing or treating graft rejection episodes.

For these indications, the appropriate dosage will, of course, vary depending upon, for example, the particular molecule of the invention to be employed, the host, the mode of administration and the nature and severity of the condition being treated. However, in prophylactic use, satisfactory results are generally indicated to be obtained at daily dosages from about 0.1 mg to about 1 mg per kilogram body weight. These dosages should be increased by up to a factor of 4 for treating a rejection event when it actually occurs. A molecule of the invention is conveniently administered parenterally, normally intravenously, for example, into the antecubital or other peripheral vein. A prophylactic treatment typically comprises administering the molecule of the invention once daily to once weekly for 2 to 4 weeks, starting on the day of transplantation, preferably some hours before transplantation.

The molecules of the invention may also be useful in the treatment of malignancies of cells expressing the CD25 antigen, for example in the treatment of T-cell leukemia and certain other leukemias and lymphomas. For this purpose, the CD25 binding molecule may be used in the form of a radioconjugate in which the molecule is coupled to an alpha-emitting radionuclide.

The molecules of the invention may also be useful in the treatment or prophylaxis of HIV infection. It appears that the HIV virus requires proliferating T cells in order to multiply, and thus inhibition of T cell proliferation by blocking the CD25 antigen should also inhibit the multiplication of the virus.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. The presence of an excess of such physiologically inert protein prevents loss of monoclonal antibody by adsorption onto the walls of the container and tubing used with the infusion solution. If albumin is used, a suitable concentration is from 0.5 to 4.5% by weight of the saline solution.

According to a further aspect of the invention, it has been found that particularly beneficial results can be achieved by the use, in combination, of at least two antigen binding molecules to activated T-cells, said binding molecules recognizing at least two different antigens characteristic of activated T-cells.

Preferably a combination of two different antigen binding molecules is used, each recognizing a different antigen. Thus although both antigen binding molecules recognize activated T-cell surface antigens, they are not competing with each other for the same binding site on activated T-cells.

Preferably one of the antigen binding molecules is a CD25 binding molecule.

Accordingly the present invention also provides an immuno suppressive composition comprising a mixture of at least one CD25 binding molecule and at least one antigen binding molecule to at least one antigen other than CD25 which is characteristic of activated T-cells.

The invention further provides at least two antigen binding molecules to activated T-cells in association with one another for use in immunosuppression of the mammalian system, said antigen binding molecules recognizing at least two different antigens characteristic of activated T-cells, one of which is the CD25 antigen.

By "antigen binding molecule to activated T-cells" is meant a binding molecule which strongly reacts with activated T-cells while it reacts weakly or not at all with resting T-cells. Preferably the antigen binding molecules are complete immunoglobulin molecules, more preferably murine, chimeric, or humanized monoclonal antibodies, particularly chimeric monoclonal antibodies. The preferred CD25 monoclonal antibodies are those having CDR's with the amino acid sequences described above.

Advantageously, the composition of the invention may also include or may be used in combination with an immunosuppressive drug such as cyclosporin A.

The preferred monoclonal antibodies to activated T-cell antigens other than CD25 are typically those classified in the CD7 cluster as established by the Boston Workshop and reported in "Leucocyte Typing II, Vol. I human T lymphocytes" by Reinherz, Haynes, Nadler and Berstein, Springer Verlag, 1985. The CD7 antigen is heterogeneously expressed on about 80% of resting T-cells. However, the expression strongly increases upon activation (a 2–3 fold rise in intensity).

A preferred combination of antibodies is therefore a combination of a CD7 with a CD25 antibody. Accordingly, the composition of the invention preferably comprises a mixture of at least one CD25 antibody together with at least one CD7 antibody, more preferably of one CD25 antibody together with one CD7 antibody. Also preferably, both antibodies are of the IgG isotype.

The two antibodies, optionally together with an immunosuppressive drug, can be used in clinical practice in various ways. Preferably they are mixed together and the physical mixture is administered to the patient. An alternative procedure is the administration of the antibodies and optionally the immunosuppressive drug to the recipient from separate reservoirs in any order but at the same time. The composition may be prepared and administered parenterally as described above for the single CD25 antibody. Alternatively, the immunosuppressive drug is administered orally and the monoclonal antibodies are administered parenterally, separately or as a mixture.

To aid in making up suitable compositions, the monoclonal antibodies and optionally an immunosuppressive drug, may be packaged separately within the same container, with instructions for mixing or concomitant administration. Examples of kits include for example a multi-barrelled syringe or a twin pack containing separate unit dose forms of at least two antibodies to activated T-cells, said antibodies recognizing at least two different antigens characteristic of activated T-cells, one of which is the CD25 antigen.

Investigations so far indicate that the administration of the antibodies in combination with one another and optionally with an immunosuppressive drug is free from unacceptable side-effects at the dosage levels employed and that there is no potentiation of the side-effects observed with the individual antibodies. For use in prophylaxis, a suitable dosage will normally call for the administration of the order of 0.05–0.5 milligram of a first antibody (such as the CD25 antibody) per kilogram body weight of the patient and 0.05–0.5 milligram of a second antibody (such as a CD7 antibody) per kilogram body weight. When the immunosuppressive drug is cyclosporin, the recommended amount of the immunosuppressive drug which can be optionally used is 2 to 5 milligram per kilogram body weight when administered parenterally and 10–15 mg/kilogram body weight when administered orally. The composition of the invention may be administered on a daily or weekly basis, preferably on a weekly basis.

Although the composition of the invention is particularly designed for use in prophylaxis of graft rejection episodes, its use can be conveniently extended to the treatment of rejection events when they actually occur. In this case, the dosages should be increased by up to a factor of 4.

Murine monoclonal antibodies suitable for use in the present invention are known per se. Many monoclonal antibodies against activated T-cell surface antigens are available from Culture Collections in various countries of the world and specifically, the American Type Culture Collection of Rockville, Md., USA can provide suitable monoclonal antibodies or hybridomas secreting such antibodies. An example of hybridoma secreting CD7 monoclonal antibodies that can be used in the present invention and that is available from the ATCC is T3-3A1. Other CD7 antibodies are RFT-2 and CHH 380 (a chimeric antibody). CD25 antibodies include, besides the preferred RFT-5 and its chimeric derivative as described above; M7/2 (Gaulton et al, Clin. Immunol. and Immunopath. (1985) 36: 18); the anti-tac antibody (Uchiyama et al, J. Immunol. (1981) 126 (4): 1393); and the Campath 6 monoclonal antibody.

The synergistic effect of a combination of CD25 and CD7 monoclonal antibodies is demonstrated in vitro by the MLR bioassay described above, and also in vivo in clinical tests on human patients.

In the MLR bioassay, inhibition of the $^3$H-TdR uptake is observed in cultures to which a CD7 (RFT2) or a CD25 (RFT5) monoclonal antibody are added singly, and there is a substantially greater degree of inhibition when both of these antibodies are used together at the same total concentration. The MLR is the in vitro equivalent of the allogeneic transplant response which leads to rejection in vivo while the inhibition described above is equivalent to immunosuppression in vivo.

In MLRs to which cyclosporin is added over a dose range from 10 nanograms/ml to 100 $\mu$g/ml, in the presence of CD7 or CD25 monoclonal antibodies there is an increased inhibition of $^3$H-TdR compared to cyclosporin alone over the whole dose range. The combination of CD7, CD25 and cyclosporin shows a greater inhibitory effect than any other combination.

In clinical tests, patients about to undergo kidney, liver or heart transplantation are selected for prophylactic therapy. On the day of transplantation, 2 hours before surgery, a first intravenous infusion of the chimeric CD25 antibody of Example 5 together with chimeric CD7 antibody (CHH 380) is administered at a dose of 0.2 mg of each antibody per kg of body weight. Two days after surgery an identical infusion of the two antibodies at 0.4 mg/kg of body weight is administered and then repeated at weekly intervals for one month.

The intravenous infusions are prepared as follows: the lyophylized antibodies are mixed together and dispersed into 100 ml sterile buffered saline containing 4.5% wt. of human albumin. This saline dispersion is administered to the patients over a 30 minute period. The patients also receive standard cyclosporin therapy. No patients undergo a rejection episode during the one month therapy period.

By way of illustration only, the production of a chimeric CD25 antibody of the invention is exemplified as follows:

EXAMPLE 1

Figure 1A:
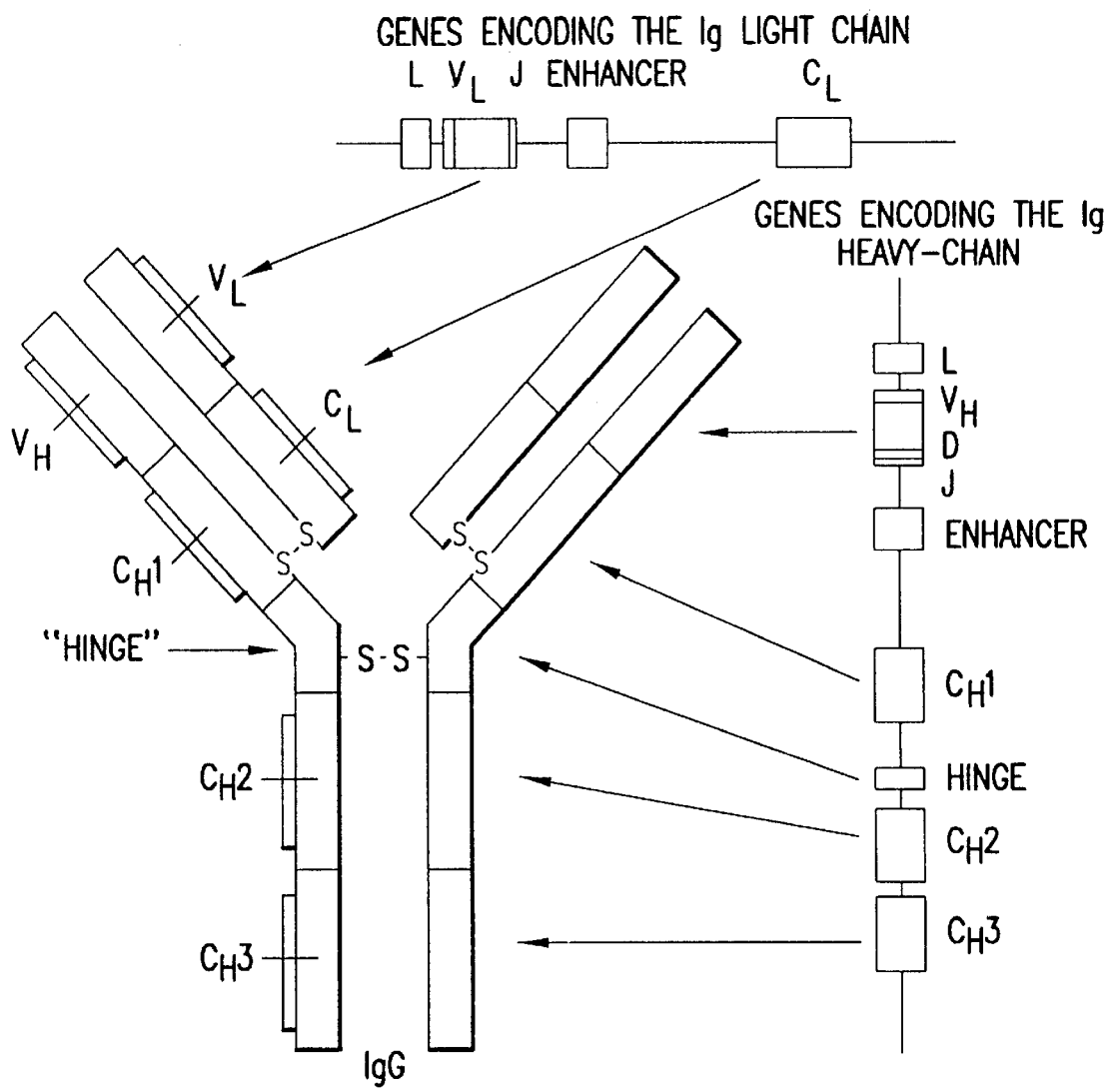
FIG. 1A is a schematic diagram showing the structure of an IgG molecule as well as the genes encoding the heavy and light chains.
Figure 1B:
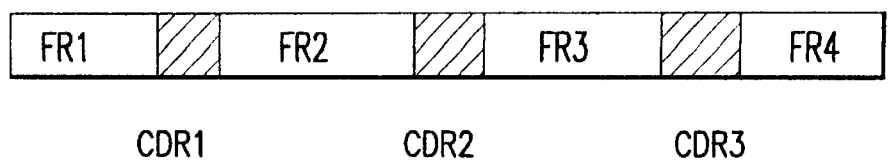
FIG. 1B schematically represents the arrangement of a variable domain of a heavy or light chain into framework (FR) and hypervariable (CDR) regions.
Figure 2A:
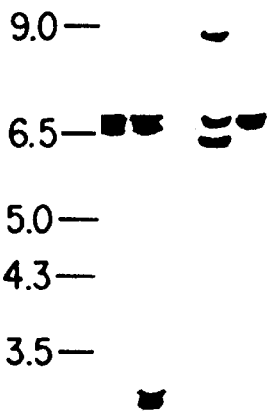
FIGS. 2A and 2B show the analysis of EcoRI-digested genomic DNA of mouse hybridoma RFT5-IgG2a (1), RFT5-IgG1 (2), RFT4 (3) and NS-1 (4) by Southern blot using a $^{32}$P labelled DNA probe either encoding the murine heavy chain enhancer (FIG. 2A) or encoding the mouse $C_\kappa$ and the five $J_\kappa$ gene segments (FIG. 2B). 10 $\mu$g of genomic DNA are digested with EcoRI and are size-fractionated on a 0.8% agarose gel. Then the fragments are transferred on a nitrocellulose membrane and hybridized with the probe. After washing, the membrane is exposed overnight on a Kodak X-0 Mat film.

Cloning of the Gene Encoding the Variable Domain of the Heavy Chain of RFT5-IgG2a The genomic DNA of the hybridomas RFT5-IgG2a (CD25; $\gamma_{2a}$; $\kappa$), RFT5-IgG1 (CD25; $\gamma_1$; $\kappa$) and RFT4 (CD4; $\gamma_1$, $\kappa$) and of the parental myeloma cell line of the hybridomas, namely NS-1, is isolated and digested with EcoRI. Each digested DNA is then fractionated on the same agarose gel. After migration, the agarose gel is analysed by Southern blot using as probe a $^{32}$P-labelled 0.7 kb XbaI-EcoRI DNA fragment which encodes the murine heavy chain enhancer (Heinrich et al, J. of Immunol. (1989) 143: 3589). 3 types of bands are revealed on the gel after hybridization as shown in FIG. 2. The 6.5 kb EcoRI fragment is present in the DNA digest of all cell lines including NS-1, the parental myeloma cell-line and therefore is of no interest. The 2.9 kb EcoRI fragment is only detected in the DNA digest of the hybridoma RFT5-IgG1 and is thought to be the result of an abnormal gene rearrangement. The 6.8 kb EcoRI fragment which is absent in the DNA digest of the parental cell line NS-1 is therefore a fragment of choice and further purification of this fragment is consequently carried out by preparative agarose gel electrophoresis.

DNA fragments of approximately 5–7 kb are cloned in the EcoRI restriction site of bacteriophage ZAP (Stratagene). Using the probe described above, 6×10$^6$ recombinant phages are screened and 11 clones are found to hybridize. The DNA insert of the 11 clones was amplified on phage plate lysate by polymerase chain reaction (PCR) using as primers, a first oligonucleotide encoding the murine $J_2$ gene and a second oligonucleotide encoding the beginning of the RFT5 heavy chain up to amino acid No. 7 (sequence previously determined). The second primer is designed taking into account the most frequent codon usage genes. The DNA fragments obtained from each of the 11 clones are analysed by Southern blot using as probe an oligonucleotide encoding the amino acid sequence comprised between amino acids 20 and 27 of the RFT5 heavy chain which is also designed according to the most frequent codon usage. 9 identical phage clones are revealed using the probe. Part of the DNA insert which encodes the variable domain is sequenced by the dideoxy termination method and is to be seen in Seq. Id. No. 1.

EXAMPLE 2

Construction of a Chimeric RFT5 Heavy Chain Gene

Figure 3A:
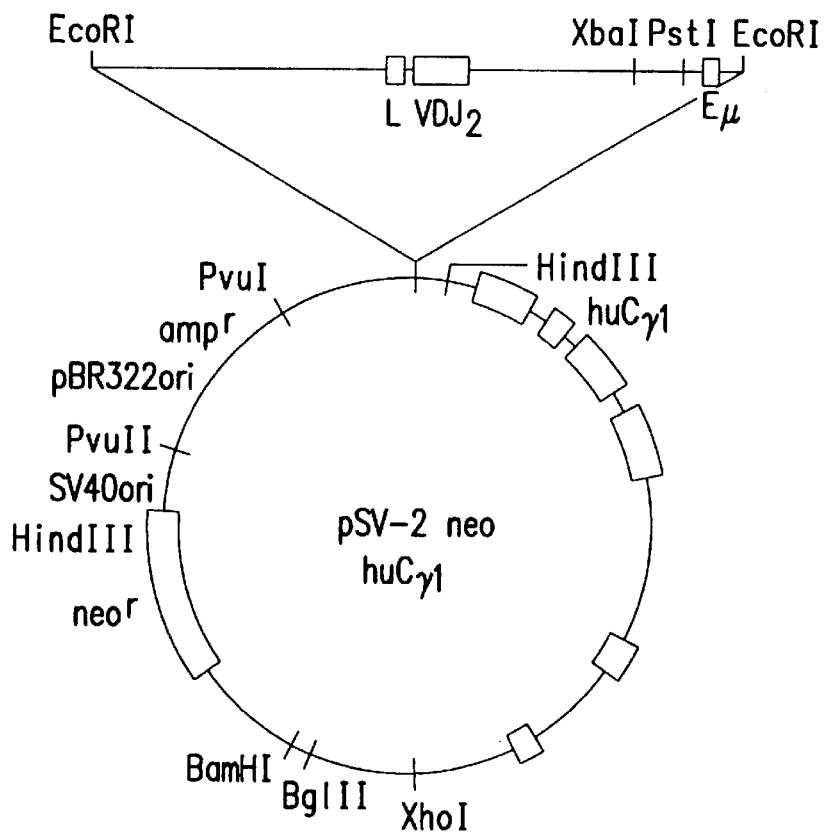
FIGS. 3A and 3B show the parental expression vectors pSV2-neo-huC$\gamma$1 and pSV2-DHFR-E$\mu$-huC$\kappa$. Both plasmids comprise an ampicillin resistance gene (amp$^R$) and the origin of replication of pBR322 and SV40 (pBR322 ori and SV40 ori). pSV2-neo-huC$\gamma$1 is characterized by the presence of a neomycin gene (neo$^R$) and the gene encoding the human $\gamma_1$ constant part (huC$\gamma_1$), while pSV2-DHFR-E$\mu$-huC$\mu$ has inserted a dihydrofolate reductase (DHFR) gene (methotrexate resistance) and the gene encoding the human $\kappa$ constant part (huC$_\kappa$). The final vectors for expressing the chimeric heavy or light chain are respectively obtained by inserting into pSV2-neo-hC$\gamma$1 a DNA fragment encoding the leader peptide (L), and the variable domain (VDJ$_2$) of the RFT5-IgG2a heavy chain together with the human heavy chain enhancer and by inserting into pSV2-DHFR-E$\mu$-huC$\kappa$ a DNA fragment encoding the leader peptide (L) and the variable domain (VJ$_2$) of the RFT5-IgG2a light chain.
Figure 3B:
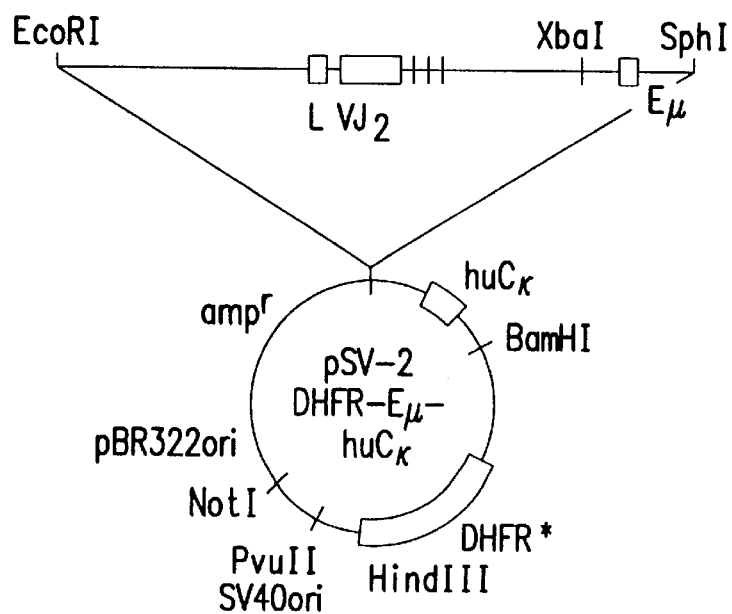

A 6 kb EcoRI fragment obtained by digestion of the DNA of one of the 9 phage clones and comprising the gene of the RFT5 heavy chain variable domain (including the promoter and the enhancer) is cloned into the EcoRI restriction site of the eukaryotic expression vector pSV2 neo-human $\gamma_1$ constant part (Heinrich et al, supra) as shown in FIG. 3A. Then the nucleotide sequence of the gene encoding the RFT5 heavy chain variable domain is redetermined to exclude the possibility that a mutation in this gene has occurred during the propagation of the plasmid.

EXAMPLE 3

Cloning of the Gene Encoding the Variable Domain of the Light Chain of RFT5

The genomic DNA of the hybridomas RFT5, RFT5* and RFT4 and of the parental cell line NS-1 is isolated and digested with EcoRI. Each digested DNA is then fractionated on the same agarose gel. After migration, the agarose gel is analysed by Southern blot using as probe a $^{32}P$ labelled DNA fragment comprising the 5 mouse $J_\kappa$ genes and the mouse $C_\kappa$ gene.

Figure 2B:
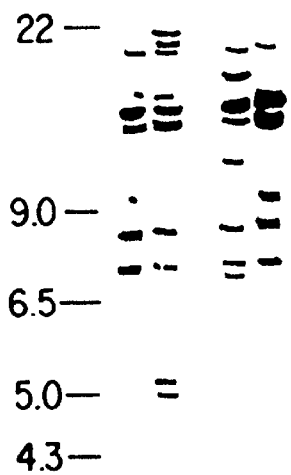

3 major types of bands of approximately 12, 16 and 18 kb are revealed on the gel after hybridization, as shown in FIG. 2B. The largest fragments are the only ones specific for the RFT5 hybridoma. Size fractionated EcoRI fragments of approximately 18 kb are cloned in phage EMBL4 (Stratagene) $7 \times 10^5$ recombinant phage clones are screened with the probe described above and 2 clones are found to hybridize each comprising an identical 18 kb insert. A 4.4 kb EcoRI-XbaI subfragment is shown to contain the full gene encoding the RFT5 light chain variable domain and is cloned into the plasmid pGEM4 (Stratagene). The sequence of the 4.4 kb fragment is determined. Part of the 4.4 kb DNA insert which encodes the variable domain is sequenced. The sequence is to be seen in Seq. Id. No. 4.

EXAMPLE 4

Construction of a Chimeric RFT5 Light Chain Gene

A 1.1 kb XbaI-XbaI fragment encoding the murine heavy chain enhancer (Heinrich et al; supra) together with a HindIII-SphI fragment encoding the human κ constant part is subcloned in phage mp18 (Stratagene). After disruption of restriction sites by mutagenesis a filled-in EcoRI-HindIII fragment comprising the sequence for the murine heavy chain enhancer (Eμ) and the human κ constant part (huCκ) is cloned in the filled in EcoRI-BamHI site of pSV2-DHFR.

pSV2-DHFR is obtained by replacing the BamHI-HindIII fragment of pSV2-neo with a BamHI-HindIII fragment encoding the DHFR gene.

The 4.4 kb EcoRI-XbaI fragment of Example 3 is then inserted into pSV2-DHFR-Eμ-hUCκ.

EXAMPLE 5

Expression of a RFT5 Chimeric Antibody

The plasmids as obtained in Examples 2 and 4 are co-transferred in the mouse myeloma cell line SP2/0 (ATCC CRL 1581) by electroporation using a gene pulser apparatus from Biorad. This technique is known to create stable transfectants at a high frequency. The SP2/0 cell line fails to produce endogeneous heavy and light chains and is sensitive to Geneticin (G 418) at a concentration of 0.8 mg/l.

SP2/0 cells are grown in the usual growth medium (RPMI+10% FCS +$5 \times 10^{-5}$ β-mercaptoethanol) harvested in the log phase of growth and washed with the electroporation buffer (Bio-Rad). Cell concentration is adjusted to $2 \times 10^7$ cells/ml. To 0.8 ml of the cell suspension is added 15–20 μg of each plasmid. The mixture is placed on ice and left to stand for 10 min. Then the cells are subjected to an electrical pulse (280 Volt; 25 μF) and again left to stand for 15 min. Cells are transferred to the usual growth medium and incubated at 37° C. in a $CO_2$ incubator.

After 3-day incubation, selection for G 418 resistance is started. Cells are resuspended in fresh medium containing 1.4 mg/ml G 418. The cultures yield growing cells after 10–14 day-incubation in the presence of G 418. After 2-week incubation, the supernatants of the confluent cultures are tested for human IgG expression in a sandwich-type ELISA (anti-human κ-light chain/supernatant/anti-human IgG-alkaline phosphatase conjugate).

This test indicates that complete antibody molecules are secreted in all cultures at varying concentrations in the range of 50–500 ng/ml.

To select cells in which the DHFR gene is amplified and therefore secrete high amounts of the desired antibody two selection procedures for Methotrexate (MTX) resistance are carried out as described below. For this purpose, the G 418 resistant cell pools are each divided and amplification is proceeded either according to procedure A (MTX increase by a factor of 2 or 2.5) or procedure B (MTX increase by a factor of 5).

| Procedure A | Procedure B |
| --- | --- |
| 100 nM MTX | 200 nM MTX |
| 250 nM MTX | 1 μM MTX |
| 500 nM MTX | 5 μM MTX |
| 1 μM MTX | 25 μM MTX |
| 2.5 μM NTX | 100 μM NTX |
| 5 μM MTX | |
| 10 μM MTX | |
| 25 μM MTX | |
| 100 μM MTX | |

Each amplification step comprises inoculating the cells at a density of $2 \times 10^5$ cells/ml in the usual growth medium supplemented with G 418 at 1.4 mg/ml and with MTX at the concentration of choice. After 72 hour incubation, cells and the supernatant are separated. Antibody secretion is monitored either by ELISA or by HPLC using a protein A column.

Figure 4A:
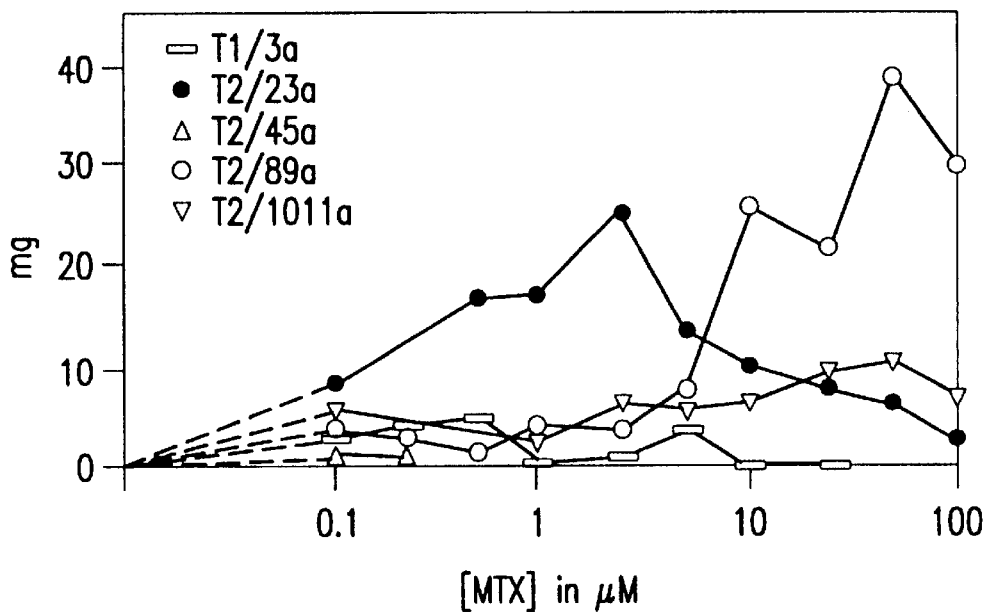
FIGS. 4A and 4B show the productivity of individual cell pools grown at increasing concentration of methotrexate (MTX) respectively according to procedures A and B described in Example 5. The Y-axis of the graph gives the amount of monoclonal antibody produced in mg/$10^9$ cells in 72 hours.
Figure 4B:
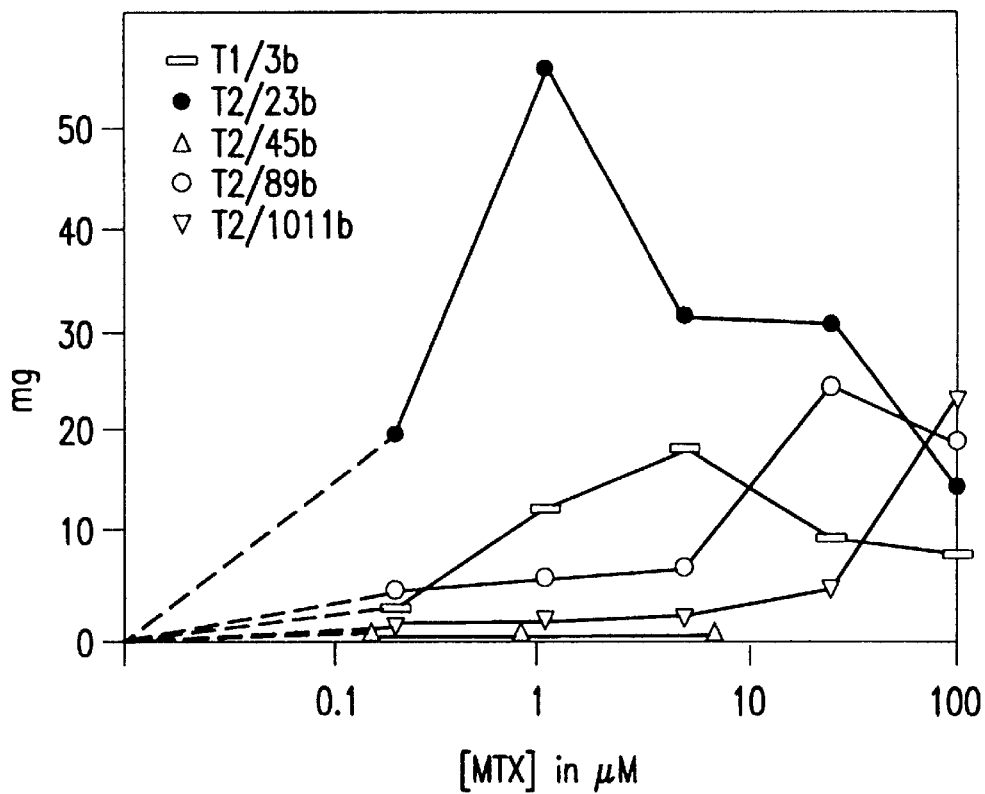
Figure 5:
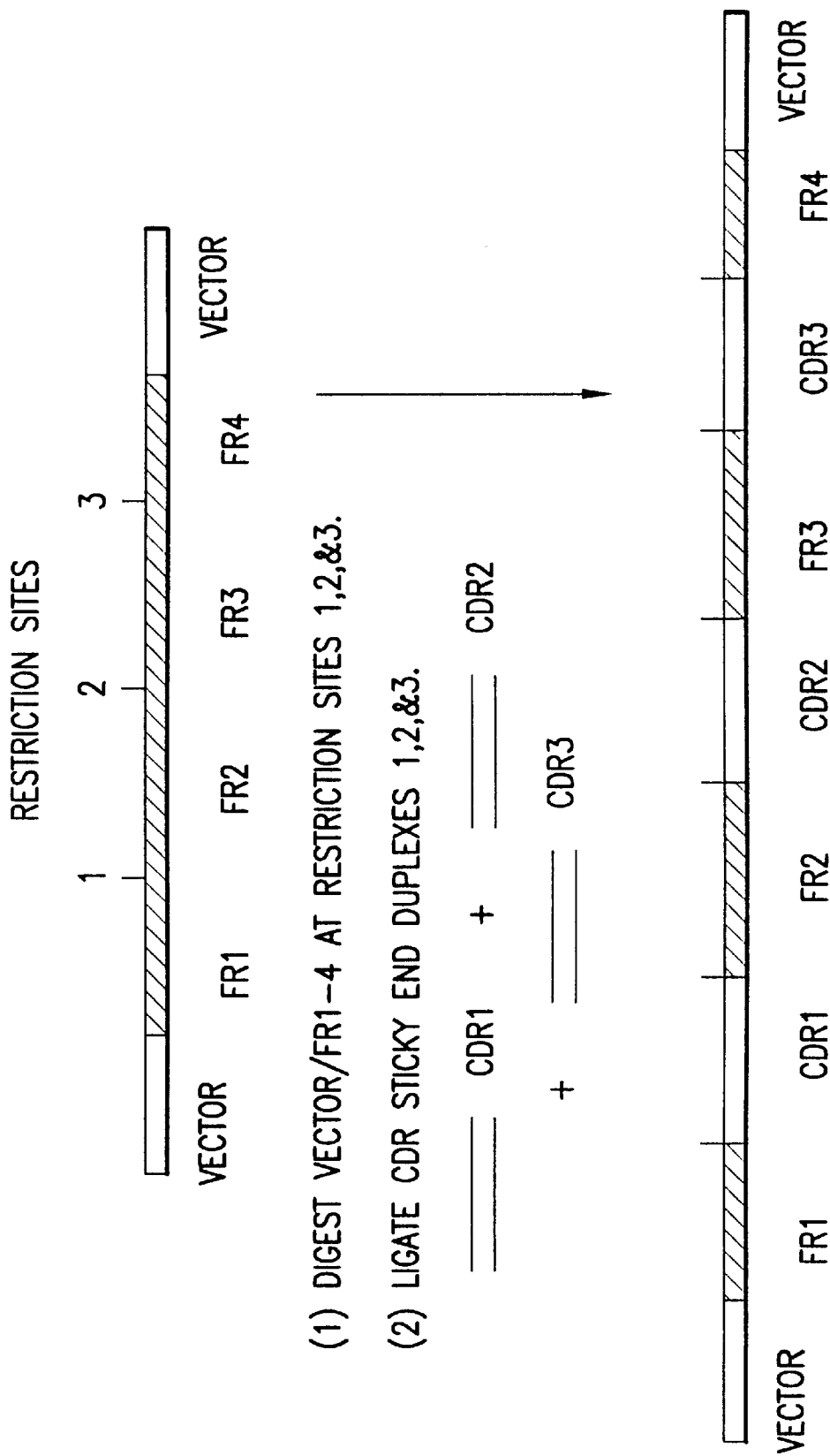
FIG. 5 shows a protocol for constructing CDR replacements by insertion of CDR cassettes into a vector containing 4 framework regions fused together.
Figure 6:
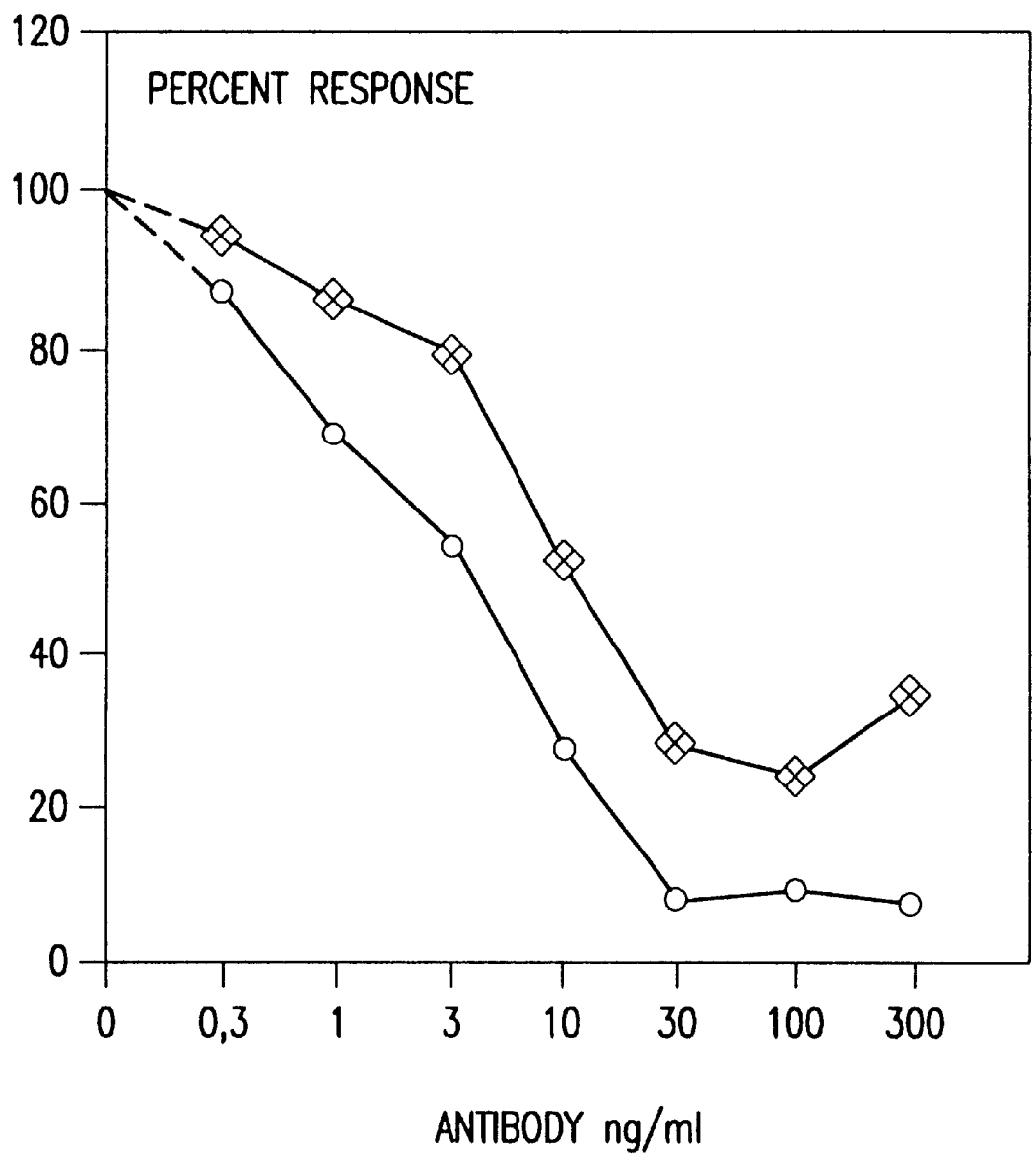
FIG. 6 shows the inhibition of MLR by (x) RFT5-IgG2a ($\gamma_2$a, $\kappa$) and (o) a murine-human chimeric MAb of the invention ($\gamma_1$, $\kappa$). Both MAbs have the variable domains as shown in Seq. Id. Nos. 3 and 6.
Figure 7:
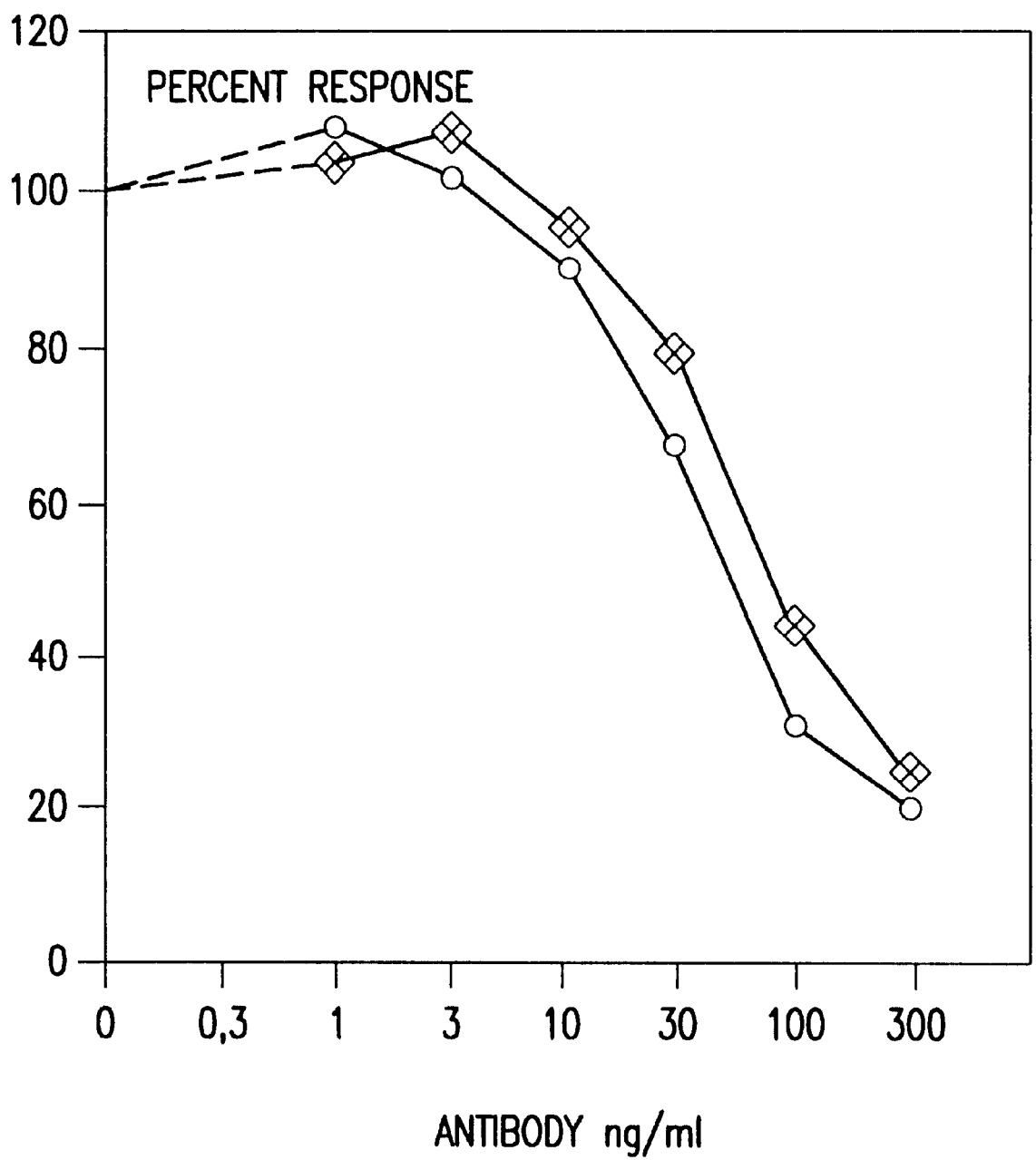
FIG. 7 shows the inhibition of PPD specific HPBM response by (x) RFT5-IgG2a and (o) the same murine-human chimeric MAb.
Figure 8A:
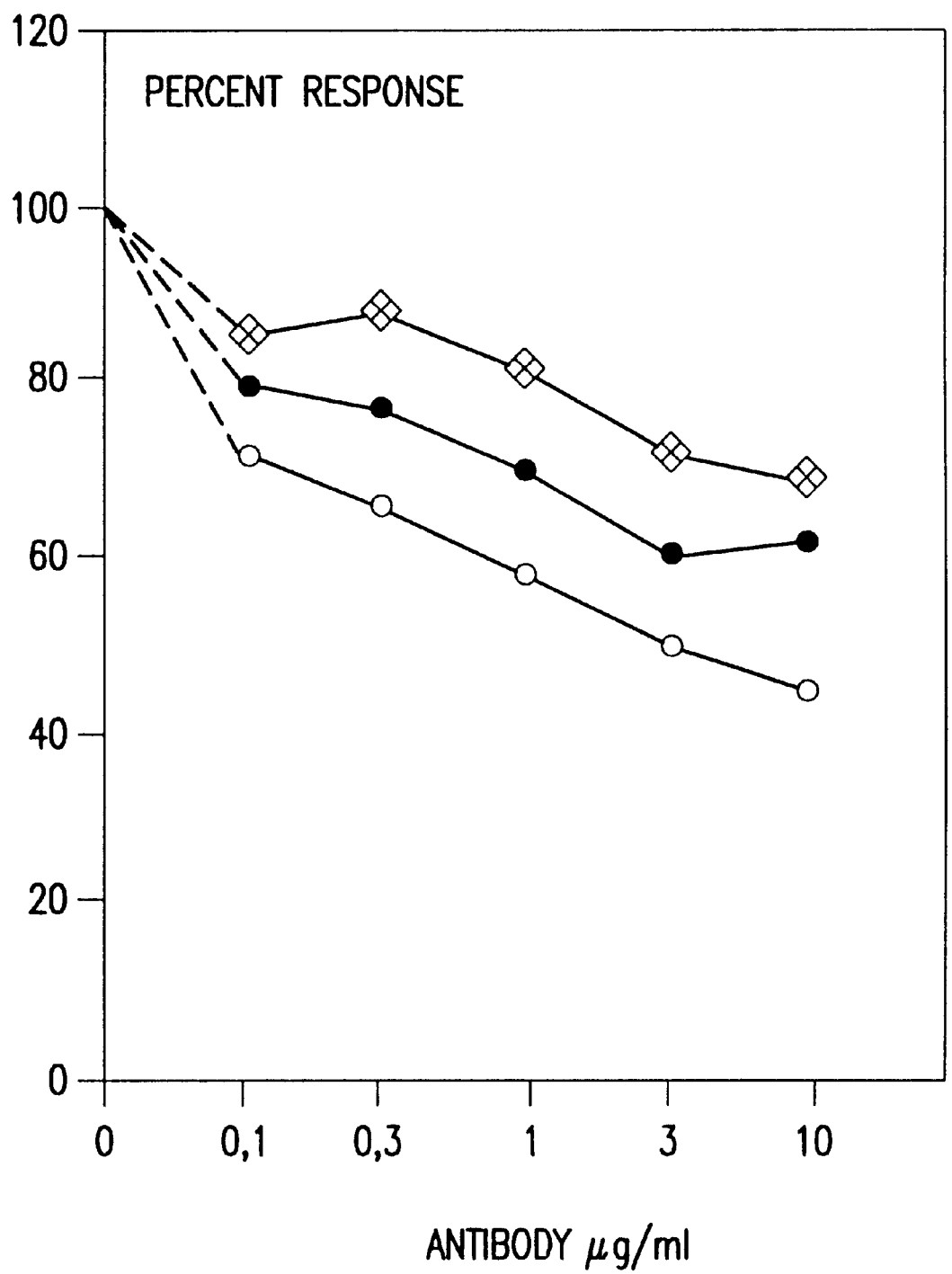
FIG. 8 shows the effect of RFT5-IgG2a and of the same murine-human chimeric MAb on PPD T-lymphoblast proliferation, (FIGS. 8B and 8A) and on MLR T-lymphoblast proliferation, (FIGS. 8D and 8C) at an IL-2 concentration of 5 ng/ml (o), 10 ng/ml ( ) and 20 ng/ml (x).
Figure 8B:
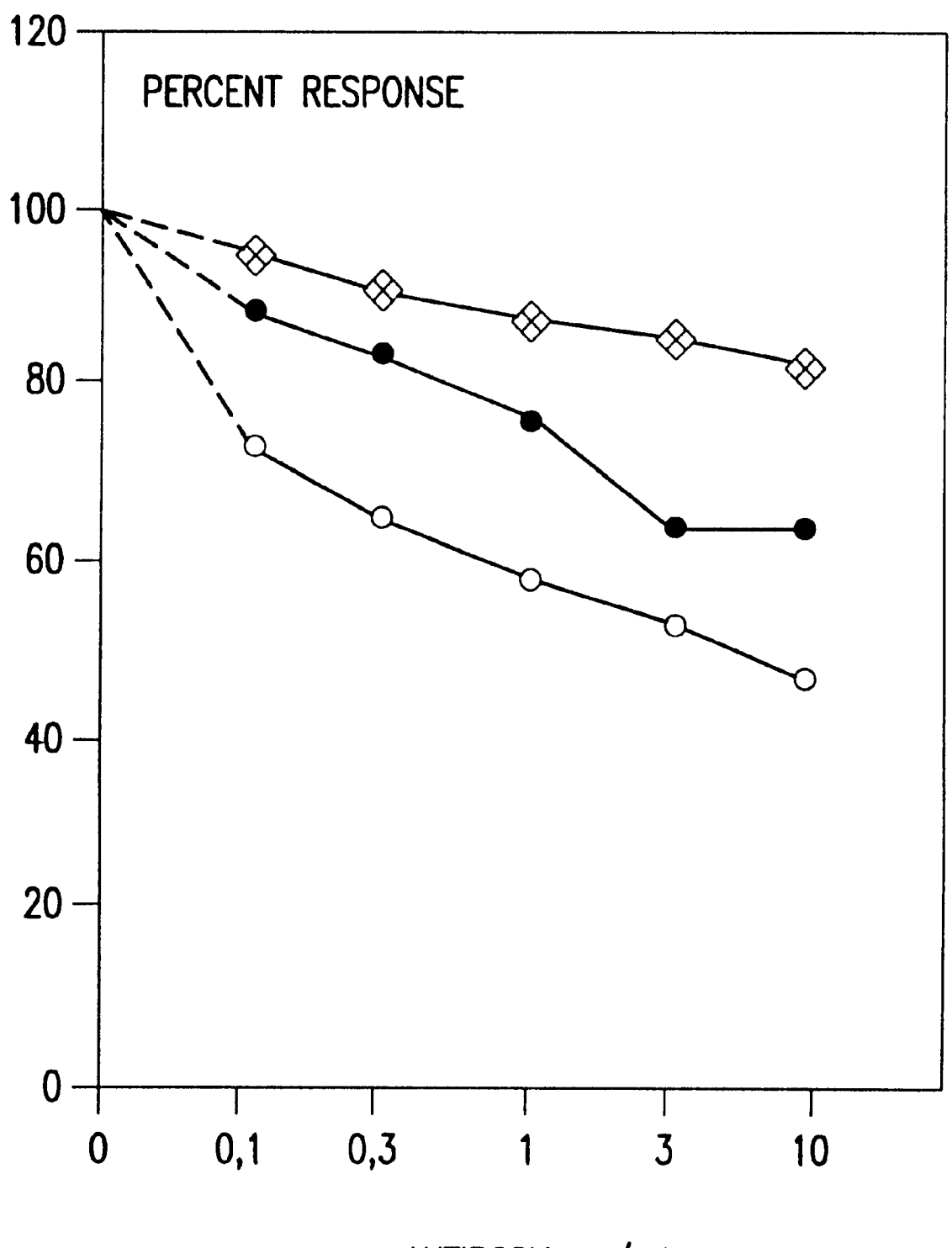
Figure 8C:
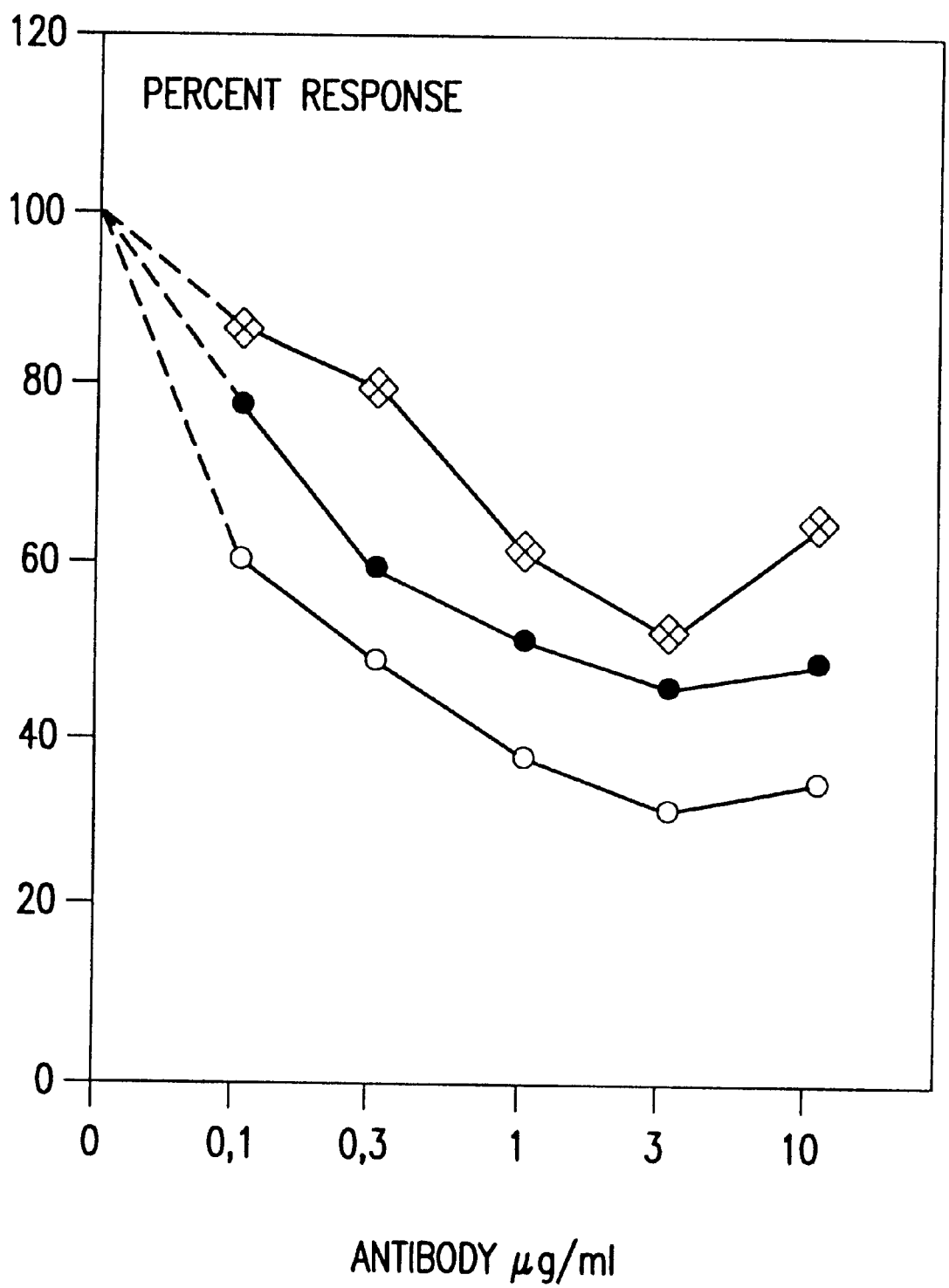
Figure 8D:
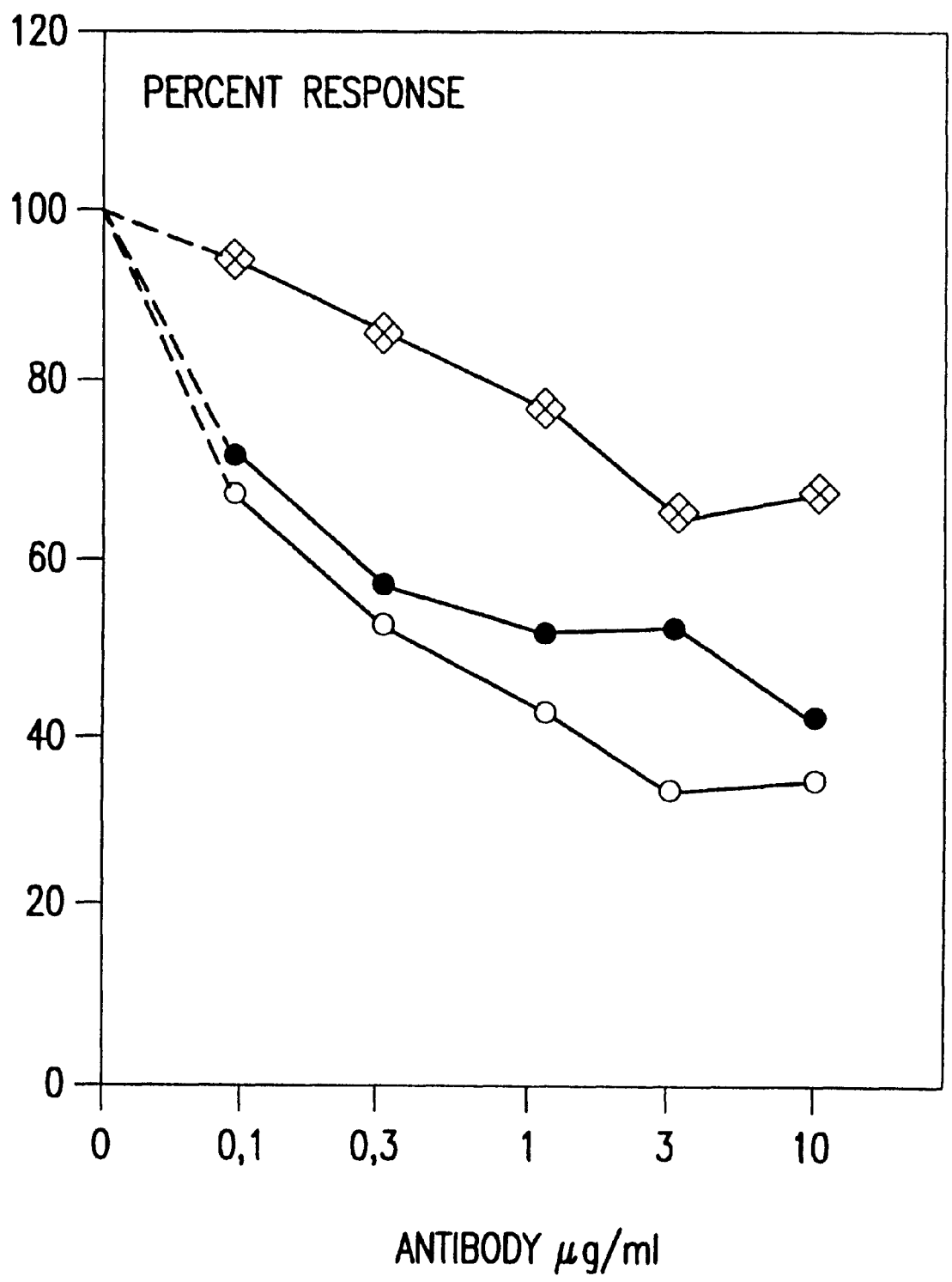

FIGS. 4A and 4B show the antibody productivity of some transfectant pools. Most of the pools reach a maximum of specific antibody production at a certain MTX concentration. The best producing pools are cloned by limiting dilution. Out of several hundred analysed clones, 15 best producing clones are selected. Productivity of the clones ranges from 30 to 50 mg MAb/$10^9$ cells in 72 hours.

The antibody is purified from a culture supernatant by elution on a protein A affinity column.

TABLE A

```
Subject matter:   The immunoglobulin heavy chain variable domain of
                  the RFT5 antibody
Sequence type:    Nucleotide sequence and its corresponding amino acid
                  sequence
Molecule type:    Genomic DNA
Length:           492 nucleotides
Original source:  A murine hybridoma
Features of the nucleotide sequence:
An intron is located from nucleotide 47 to 130
    V segment gene:   from nucleotide 142 to 435 of SEQ. ID. NO.1
    D segment gene:   from nucleotide 436 to 447 of SEQ. ID. NO.1
    J segment gene:   from nucleotide 448 to 492 of SEQ. ID. NO.1
Features of the amino acid sequence:
Leader peptide: from amino acid (a.a.) -19 to -1
FR1:    from a.a. 1 to 30 of SEQ. ID. NO.1
CDR1:   from a.a. 31 to 35 of SEQ. ID. NO.1(i.e. SEQ. ID. NO.7)
FR2:    from a.a. 36 to 49 of SEQ. ID. NO.1
CDR2:   from a.a. 50 to 66 of SEQ. ID. NO.1(i.e. SEQ. ID. NO.8)
FR3:    from a.a. 67 to 98 of SEQ. ID. NO.1
CDR3:   from a.a. 99 to 106 of SEQ. ID. NO.1(i.e. SEQ. ID. NO.9)
FR4:    from a.a. 107 to 177 of SEQ. ID. NO.1
ATG GAA TGT AAC TGG ATA CTT CCT TTT ATT CTG TCG GTA ATT TCA G         46

Met Glu Cys Asn Trp Ile Leu Pro Phe Ile Leu Ser Val Ile Ser
              -15              -10             -5

GTAAGGGGCT CACCAGTTCC ATATCTGAAA GAGGATACAG GGTCTGAAGT GACAATGACA    106

TCTACTCTGC TGTTCTCTCC ACAG    GG GTC TAC TCA GAG GTT CAG CTC CAG    156

Gly Val Tyr Ser Glu Val Gln Leu Gln
                                              -1   1               5

CAG TCT GGG ACT GTG CTG GCT AGG CCT GGG GCT TCC GTG AAG ATG TCC     204

Gln Ser Gly Thr Val Leu Ala Arg Pro Gly Ala Ser Val Lys Met Ser
             10              15              20

TGC AAG GCT TCT GGC TAC AGC TTT ACC AGG TAC TGG ATG CAC TGG ATA     252

Cys Lys Ala Ser Gly Tyr Ser Phe Thr Arg Tyr Trp Met His Trp Ile
             25              30              35

AAA CAG AGG CCT GGA CAG GGT CTA GAA TGG ATT GGT GCT ATT TAT CCT     300

Lys Gln Arg Pro Gly Gln Gly Leu Glu Trp Ile Gly Ala Ile Tyr Pro
             40              45              50

GGA AAT AGT GAT ACT AGT TAC AAC CAG AAG TTC GAG GGC AAG GCC AAA     348

Gly Asn Ser Asp Thr Ser Tyr Asn Gln Lys Phe Glu Gly Lys Ala Lys
             55              60              65

CTG ACT GCA GTC ACA TCC GCC AGC ACT GCC TAC ATG GAG CTC AGC AGC     396

Leu Thr Ala Val Thr Ser Ala Ser Thr Ala Tyr Met Glu Leu Ser Ser
    70              75              80                      85

CTG ACA CAT GAG GAC TCT GCG GTC TAT TAC TGT TCA AGA GAC TAC GGC     444

Leu Thr His Glu Asp Ser Ala Val Tyr Tyr Cys Ser Arg Asp Tyr Gly
                 90              95                      100

TAC TAC TTT GAC TTC TGG GGC CAA GGC ACC ACT CTC ACA GTC TCC TCA     492

Tyr Tyr Phe Asp Phe Trp Gly Gln Gly Thr Thr Leu Thr Val Ser Ser
             105             110             115
```

TABLE B

Subject matter: The immunoglobulin light chain variable domain of the RFT5 antibody
Sequence type: Nucleotide sequence and its corresponding amino acid sequence
Molecule type: Genomic DNA
Length: 555 nucleotides
Original source: A murine hybridoma
Features of the nucleotide sequence:
An intron is located from nucleotide 50 to 226
   V segment gene:
   from nucleotide
   244 to 519 of SEQ.
   ID. NO.4
   J2 segment gene:
   from nucleotide
   520 to 555 of SEQ.
   ID. NO.4
Features of the amino acid sequence:
leader   from a.a. -22 to -1 of SEQ. ID. NO.4
peptide:
FR1':    from a.a. 1 to 23 of SEQ. ID. NO.4
CDR1':   from a.a. 24 to 33 of SEQ. ID. NO.4(i.e. SEQ.ID. NO.10)
FR2':    from a.a. 34 to 48 of SEQ. ID. NO.4
CDR2':   from a.a. 49 to 55 of SEQ. ID. NO.4(i.e. SEQ. ID. NO.11)
FR3':    from a.a. 56 to 87 of SEQ. ID. NO.4
CDR3':   from a.a. 88 to 94 of SEQ. ID. NO.4(i.e. SEQ. ID. NO.12)
FR4':    from a.a. 95 to 104 of SEQ. ID. NO.4

```
ATG GAT TTT CAG GTG CAG ATT TTC AGC TTC CTG CTA ATC AGT GCC TCA G    49

Met Asp Phe Gln Val Gln Ile Phe Ser Phe Leu Leu Ile Ser Ala Ser
        -20              -15              -10

GTAACAGAGG GCAGGGAATT TGAGATCAGA ATCCAACCAA AATTATTTTC CCTGGGGAAT   109

TTGAGTCTAA AATACAGTTT TTTTTTCTTT TTCTTCATCT GAATGTTGGG TGGTATAAAA   169

TTATTTTTGT TTCTCTATTT CTACTAATCC CTTTCTCTCT ATTTTGCTTT TTTCTAG      226

TC ATA CTG TCC AGA GGA CAA ATT GTT CTC ACC CAG TCT CCA GCA ATC     273

Val Ile Leu Ser Arg Gly Gln Ile Val Leu Thr Gln Ser Pro Ala Ile
     -5              -1   1              5                     10

ATG TCT GCA TCT CCA GGG GAG AAG GTC ACC ATG ACC TGC AGT GCC AGC     321

Met Ser Ala Ser Pro Gly Glu Lys Val Thr Met Thr Cys Ser Ala Ser
                15                  20                  25

TCA AGT ATA AGT TAC ATG CAG TGG TAC CAG CAG AAG CCA GGC ACC TCC     369

Ser Ser Ile Ser Tyr Met Gln Trp Tyr Gln Gln Lys Pro Gly Thr Ser
             30                  35                  40

CCC AAA AGA TGG ATT TAT GAC ACA TCC AAA CTG GCT TCT GGA GTC CCT     417

Pro Lys Arg Trp Ile Tyr Asp Thr Ser Lys Leu Ala Ser Gly Val Pro
         45                  50                  55

GCT CGC TTC AGT GGC AGT GGG TCT GGG ACC TCT TAT TCT CTC ACA ATC     465

Ala Arg Phe Ser Gly Ser Gly Ser Gly Thr Ser Tyr Ser Leu Thr Ile
     60                  65                  70

AGC AGC ATG GAG GCTGAAGAT GCT GCC ACT TAT TAC TGC CAT CA4 CGG       513

Ser Ser Met Glu Ala Glu Asp Ala Ala Thr Tyr Tyr Cys His Gln Arg
75                  80                  85                  90

AGT AGT TAC ACG TTC GGA GGG GGG ACC AAA CTG GAA ATA AAA             555

Ser Ser Tyr Thr Phe Gly Gly Gly Thr Lys Leu Glu Ile Lys
                 95                 100
```

TABLE C

| Region | Location on the heavy chain | Location on the light chain |
| --- | --- | --- |
| FR1 | amino acid 1 to 30 (with an occasional residue at 0) | amino acid 1 to 23 (with an occasional residue at 0 and a deletion at 10 in λ chains) |
| CDR1 | amino acid 31 to 35 (with possible insertions numbered as 35A, 35B) | amino acid 24 to 34 (with possible insertion numbered as 27A, B, C, D, E and F) |
| FR2 | amino acid 36 to 49 | amino acid 35 to 49 |
| CDR2 | amino acid 50 to 65 (with possible insertions numbered as 52A, B and C) | amino acid 50 to 56 |
| FR3 | amino acid 66 to 94 (with possible insertions numbered 82A, B and C) | amino acid 57 to 88 |
| CDR3 | amino acid 95 to 102 (with possible insertions numbered as 100A, B, C, D, E, F, G, H, I, J, and K) | amino acid 89 to 97 (with possible insertions numbered as 95A, B, C, D, E and F) |
| FR4 | amino acid 103 to 113 | amino acid 98–107 (with a possible insertion numbered as 106A) |

What is claimed is:

1. A method of treating lymphomas or T-cell leukemias in a patient in need of such treatment comprising administering to the patient an effective amount of a conjugate of a CD25 binding molecule and an enzyme, toxin or radioisotope, which CD25 binding molecule comprises:

at least one antigen binding site comprising at least one domain which comprises in sequence hypervariable regions CDR1, CDR2 and CDR3, said hypervariable regions alternating with framework regions, wherein said CDR1 comprises the amino acid sequence in SEQ. ID. NO: 7, said CDR2 comprises the amino acid sequence in SEQ. ID. NO: 8 and said CDR3 comprises the amino acid sequence in SEQ. ID. NO: 9; or said CDR1, COR2 and CDR3 taken in sequence as a whole comprise an amino acid sequence which is at least 90% identical to SEQ. ID. NOs: 7, 8 and 9 taken in sequence as a whole.

2. A method according to claim 1 wherein said CDR1 comprises the amino acid sequence in SEQ. ID. NO: 7, said CDR2 comprises the amino acid sequence in SEQ. ID. NO: 8 and said CDR3 comprises the amino acid sequence in SEQ. ID. NO: 9.

3. A method according to claim 2 wherein said CDR1 consists of the amino acid sequence in SEQ. ID. NO: 7, said CDR2 consists of the amino acid sequence in SEQ. ID. NO: 8 and said CDR3 consists of the amino acid sequence in SEQ. ID. NO: 9.

4. A method according to claim 1 wherein said CD25 binding molecule comprises at least one antigen binding site which comprises at least one domain which comprises the amino acid sequence in SEQ. ID. NO: 3.

5. A method according to claim 4 wherein said CD25 binding molecule comprises a single antigen binding site consisting of the amino acid sequence in SEQ. ID. NO: 3.

6. A method of treating lymphomas or T-cell leukemias in a patient in need of such treatment comprising administering to the patient an effective amount of a conjugate of a CD25 binding molecule and an enzyme, toxin or radioisotope, which CD25 binding molecule comprises at least one antigen binding site comprising:

(a) a first domain comprising in sequence hypervariable regions CDR1, CDR2 and CDR3, said hypervariable regions alternating with framework regions, and (b) a second domain comprising in sequence hypervariable regions CDR1', CDR2' and CDR3', said hypervariable regions alternating with framework regions, wherein said CDR1 comprises the amino acid sequence in SEQ. ID. NO: 7, said CDR2 comprises the damino acid sequence in SEQ. ID. NO: 8, said CDR3 comprises the amino acid sequence in SEQ. ID. NO: 9, said CDR1' comprises the amino acid sequence in SEQ. ID. NO: 10, said CDR2' comprises the amino acid sequence in SEQ. ID. NO: 11, and said CDR3' comprises the amino acid sequence in SEQ. ID. NO: 12; or said CDR1, CDR2, CDR3, CDR1', CDR2' and CDR3' taken in sequence as a whole comprise an amino acid sequence which is at least 95% identical to SEQ. ID. Nos. 7, 8, 9, 10, 11 and 12 taken in sequence as a whole.

7. A method according to claim 6 wherein said CDR1 comprises the amino acid sequence in SEQ. ID. NO: 7, said CDR2 comprises the amino acid sequence in SEQ. ID. NO: 8, said CDR3 comprises the amino acid sequence in SEQ. ID. NO: 9, said CDR1' comprises the amino acid sequence in SEQ. ID. NO: 10, said CDR2' comprises the amino acid sequence in SEQ. ID. NO: 11, and said CDR3' comprises the amino acid sequence in SEQ. ID. NO: 12.

8. A method according to claim 7 wherein said CDR1 consists of the amino acid sequence in SEQ. ID. NO: 7, said CDR2 consists of the amino acid sequence in SEQ. ID. NO: 8, said CDR3 consists of the amino acid sequence in SEQ. ID. NO: 9, said CDR1' consists of the amino acio sequence in SEQ. ID. NO: 10, said CDR2' consists of the amino acid sequence in SEQ. ID. NO: 11 and said CDR3' consists of the amino acid sequence in SEQ. ID. NO: 12.

9. A method according to claim 6 wherein the first domain comprises the amino acid sequence in SEQ. ID. NO: 3 and the second domain comprises the amino acid sequence in SEQ. ID. NO: 6.

10. A method according to claim 9 wherein the first domain consists of the amino acid sequence in SEQ. ID. NO: 3 and the second domain consists of the amino acid sequence in SEQ. ID. NO: 6.

11. A method of treating lymphomas or T-cell leukemias in a patient in need of such treatment comprising administering to the patient an effective amount of a conjugate of a single chain CD25 binding molecule and an enzyme, toxin or radioisotope, which single chain CD25 binding molecule comprises at least one antigen binding site comprising;

(a) a first domain comprising in sequence hypervariable regions CDR1, CDR2 and CDR3, said hypervariable regions alternating with framework regions, (b) a second domain comprising in sequence hypervariable regions CDR1', CDR2' and CDR3', said hypervariable regions alternating with framework regions, and (c) a peptide linker which is bound either to the N-terminus of the first domain and the C-terminus of the second domain or to the C-terminus of the first domain and the N-terminus of the second domain, wherein said CDR1 comprises the amino acid sequence in SEQ. ID. NO: 7, said CDR2 comprises the amino acid sequence in SEQ. ID. NO: 8, said CDR3 comprises the amino acid sequence in SEQ. ID. NO: 9, said CDR1' comprises the amino acid sequence in SEQ. ID. NO: 10, said CDR2' comprises the amino acid sequence in SEQ. ID. NO: 11, and said CDR3' comprises the amino acid sequence in SEQ. ID. NO: 12; or said CDR1, CDR2, CDR3, CDR1', CDR2' and CDR3' taken in sequence as a whole comprise an amino acid sequence which is at least 90% identical to SEQ. ID. Nos. 7, 8, 9, 10, 11 and 12 taken in sequence as a whole.

12. A method according to claim 11 wherein said CDR1 comprises the amino acid sequence in SEQ. ID. NO: 7, said CDR2 comprises the amino acid sequence in SEQ. ID. NO: 8, said CDR3 comprises the amino acid sequence in SEQ. ID. NO: 9, said CDR1' comprises the amino acid sequence in SEQ. ID. NO: 10, said CDR2' comprises the amino acid sequence in SEQ. ID. NO: 11, and said CDR3' comprises the amino acid sequence in SEQ. ID. NO: 12.

13. A method according to claim 11 wherein the first domain comprises the amino acid sequence in SEQ. ID. NO: 3 and the second domain comprises the amino acid sequence in SEQ. ID. NO: 6.

14. A method according to claim 13 wherein the first domain consists of the amino acid sequence in SEQ. ID. NO: 3, the second domain consists of the amino acid sequence in SEQ. ID. NO: 6, and the peptide linker consists of from 10 to 30 amino acids.

15. A method of treating lymphomas or T-cell leukemias in a patient in need of such treatment comprising administering to the patient an effective amount of a conjugate of a CD25 binding moledule and an enzyme, toxin or radioisotope, which CD25 binding molecule comprises:

(a) an immunoglobulin heavy chain or fragment thereof which comprises (i) a variable domain comprising in sequence hypervariable regions CDR1, CDR2 and CDR3, said hypervariable regions alternating with framework regions, and (ii) the constant part or fragment thereof of a human heavy chain; and (b) an immunoglobulin light chain or fragment thereof which comprises (i) a variable domain comprising in sequence hypervariable regions CDR1', CDR2' and CDR3', said hypervariable regions alternating with framework regions, and (ii) the constant part or fragment thereof of a human light chain,
wherein said CDR1 comprises the amino acid sequence in SEQ. ID. NO: 7, said CDR2 comprises the amino acid sequence in SEQ. ID. NO: 8, said CDR3 comprises the amino acid sequence in SEQ. ID. NO: 9, said CDR1' comprises the amino acid sequence in SEQ. ID. NO: 10, said CDR2' comprises the amino acid sequence in SEQ. ID. NO: 11, and said CDR3' comprises the amino acid sequence in SEQ. ID. NO: 12: or said CDR1, CDR2, CDR3, CDR1', CDR2' and CDR3' taken in sequence as a whole comprise an amino acid sequence which is at least 90% identical to SEQ. ID. Nos. 7, 8, 9, 10, 11 and 12 taken in sequence as a whole.

16. A method according to claim 15 wherein said CDR1 comprises the amino acid sequence in SEQ. ID. NO: 7, said CDR2 comprises the amino acid sequence in SEQ. ID. NO: 8, said CDR3 comprises the amino acid sequence in SEQ. ID. NO: 9, said CDR1' comprises the amino acid'sequence in SEQ. ID. NO: 10, said CDR2' comprises the amino acid sequence in SEQ. ID. NO: 11, and said CDR3' comprises the amino acid sequence in SEQ. ID. NO: 12.

17. A method according to claim 16 wherein said CDR1 consists of the amino acid sequence in SEQ. ID. NO: 7, said CDR2 consists of the amino acid sequence in SEQ. ID. NO: 8, said CDR3 consists of the amino acid sequence in SEQ. ID. NO: 9, said CDR1' consists of the amino aced sequence in SEQ. ID. NO: 10, said CDR2' consists of the amino acid sequence in SEQ. ID. NO: 11, and said CDR3' consists of the amino acid sequence in SEQ. ID. NO: 12.

18. A method according to claim 15 wherein the constant part or fragment thereof of the human heavy chain is of the γ type.

19. A method according to claim 16 wherein the constant part or fragment thereof of the human heavy chain is of the γ type.

20. A method according to claim 19 wherein the constant part or fragment thereof of the human light chain is of the κ type.

21. A method according to claim 15 wherein the immunoglobulin heavy chain or fragment thereof comprises a variable domain comprising the amino acid sequence in SEQ. ID. NO: 3 and the immunoglobulin light chain or fragment thereof comprises a variable domain comprising the amino acid sequence in SEQ. ID. NO: 6.

22. A method according to claim 21 wherein the constant part or fragment thereof of the human heavy chain is of the γ type.

23. A method according to claim 22 wherein the constant part or fragment thereof of the human light chain is of the κ type.

24. A method according to claim 21 wherein the variable domain of the immunoglobulin heavy chain or fragment thereof consists of the amino acid sequence in SEQ. ID. NO: 3 and the variable domain of the immunoglobulin light chain or fragment thereof consists of the amino acid sequence in SEQ. ID. NO: 6.

25. A method of treating lymphomas in a patient in need of such treatment comprising administering to the patient an effective amount of a conjugate of a CD25 binding molecule and an enzyme, toxin or radioisotope, which CD25 binding molecule comprises:
(a) an immunoglobulin heavy chain or fragment thereof which consists of the amino acid sequence in SEQ. ID. NO: 3 and the constant part or fragment thereof of a human heavy chain of the γ type, and
(b) an immunoglobulin light chain or fragment thereof which consists of the amino acid sequence in SEQ. ID. NO: 6 and the constant part or fragment thereof of a human light chain of the κ type.

26. A method of treating T-cell leukemias in a patient in need of such treatment comprising administering to the patient an effective amount of a conjugate of a CD25 binding molecule and an enzyme, toxin or radioisotope, which CD25 binding molecule comprises:
(a) an immunoglobulin heavy chain or fragment thereof which consists of the amino acid sequence in SEQ. ID. NO: 3 and the constant part or fragment thereof of a human heavy chain of the γ type, and
(b) an immunoglobulin light chain or fragment thereof which consists of the amino acid sequence in SEQ. ID. NO: 6 and the constant part or fragment thereof of a human light chain of the κ type.

27. A method of treating malignancies of cells expressing the CD25 antigen in a patient in need of such treatment comprising administering to the patient an effective amount of a conjugate of a CD25 binding molecule and an enzyme, toxin or radioisotope, which CD25 binding molecule comprises:
(a) an immunoglobulin heavy chain or fragment thereof which consists of the amino acid sequence in SEQ. ID. NO: 3 and the constant part or fragment thereof of a human heavy chain of the γ type, and
(b) an immunoglobulin light chain or fragment thereof which consists of the amino acid sequence in SEQ. ID. NO: 6 and the constant part or fragment thereof of a human light chain of the κ type.

28. A method according to claims 25, 26 or 27 wherein the CD25 binding molecule consists of:
(a) two disulfide bonded immunoglobulin heavy chains consisting of the amino acid sequence in SEQ. ID. NO: 3 and the constant part of a human heavy chain of the $\gamma_1$ type, and
(b) two immunoglobulin light chains consisting of the amino acid sequence in SEQ. ID. NO: 6 and the constant part of a human light chain of the κ type, each immunoglobulin light chain being linked by disulfide bonding to a different immunoglobulin heavy chain of (a).

29. A method according to claims 25, 26 or 27 wherein the CD25 binding molecule consists of:
(a) two immunoglobulin heavy chains consisting of the amino acid sequence in SEQ. ID. NO:3 and the constant part of a human heavy chain of the γ type, and
(b) two immunoglobulin light chains consisting of the amino acid sequence in SEQ. ID. NO:6 and the constant part of a human light chain of the k type.

* * * * *

UNITED STATES PATENT AND TRADEMARK OFFICE
CERTIFICATE OF CORRECTION

PATENT NO. : 6,383,487 B1
DATED : May 7, 2002
INVENTOR(S) : Amlot et al.

It is certified that error appears in the above-identified patent and that said Letters Patent is hereby corrected as shown below:

<u>Column 35,</u>
Line 36, should read -- in SEQ. ID. NO: 7, said CDR2 comprises the amino --
Line 60, should read -- ID. NO: 9, said CDR1' consists of the amino acid sequence --

<u>Column 37,</u>
Line 10, should read -- sequence in SEQ. ID. NO: 12; or said CDR1, --
Line 21, should read -- ID. NO: 9, said CDR1' comprises the amino acid sequence --
Line 29, should read -- ID. NO: 9, said CDR1' consists of the amino acid sequence --

Signed and Sealed this

First Day of July, 2003

JAMES E. ROGAN
*Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 492 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 142..492

(ix) FEATURE:
      (A) NAME/KEY: sig_peptide
      (B) LOCATION: 1..141

(ix) FEATURE:
      (A) NAME/KEY: intron
      (B) LOCATION: 47..130

(ix) FEATURE:
      (A) NAME/KEY: misc_feature
      (B) LOCATION: 142..435
      (D) OTHER INFORMATION: /standard_name= "V SEGMENT GENE"

(ix) FEATURE:
      (A) NAME/KEY: misc_feature
      (B) LOCATION: 436..447
      (D) OTHER INFORMATION: /standard_name= "D SEGMENT GENE"

(ix) FEATURE:
      (A) NAME/KEY: misc_feature
      (B) LOCATION: 448..492
      (D) OTHER INFORMATION: /standard_name= "J SEGMENT GENE"

(xi) SEQUENCE DESCRIPTION: SEQ ID NO:1:

```
ATGGAATGTA ACTGGATACT TCCTTTTATT CTGTCGGTAA TTTCAGGTAA GGGGCTCACC      60
AGTTCCATAT CTGAAAGAGG ATACAGGGTC TGAAGTGACA ATGACATCTA CTCTGCTGTT     120
```

-continued

```
CTCTCCACAG GGGTCTACTC A GAG GTT CAG CTC CAG CAG TCT GGG ACT GTG      171
                        Glu Val Gln Leu Gln Gln Ser Gly Thr Val
                         1               5                      10

CTG GCT AGG CCT GGG GCT TCC GTG AAG ATG TCC TGC AAG GCT TCT GGC      219
Leu Ala Arg Pro Gly Ala Ser Val Lys Met Ser Cys Lys Ala Ser Gly
                15                  20                  25

TAC AGC TTT ACC AGG TAC TGG ATG CAC TGG ATA AAA CAG AGG CCT GGA      267
Tyr Ser Phe Thr Arg Tyr Trp Met His Trp Ile Lys Gln Arg Pro Gly
             30                  35                  40

CAG GGT CTA GAA TGG ATT GGT GCT ATT TAT CCT GGA AAT AGT GAT ACT      315
Gln Gly Leu Glu Trp Ile Gly Ala Ile Tyr Pro Gly Asn Ser Asp Thr
         45                  50                  55

AGT TAC AAC CAG AAG TTC GAG GGC AAG GCC AAA CTG ACT GCA GTC ACA      363
Ser Tyr Asn Gln Lys Phe Glu Gly Lys Ala Lys Leu Thr Ala Val Thr
     60                  65                  70

TCC GCC AGC ACT GCC TAC ATG GAG CTC AGC AGC CTG ACA CAT GAG GAC      411
Ser Ala Ser Thr Ala Tyr Met Glu Leu Ser Ser Leu Thr His Glu Asp
 75                  80                  85                  90

TCT GCG GTC TAT TAC TGT TCA AGA GAC TAC GGC TAC TAC TTT GAC TTC      459
Ser Ala Val Tyr Tyr Cys Ser Arg Asp Tyr Gly Tyr Tyr Phe Asp Phe
                 95                 100                 105

TGG GGC CAA GGC ACC ACT CTC ACA GTC TCC TCA                          492
Trp Gly Gln Gly Thr Thr Leu Thr Val Ser Ser
            110                 115
```

(2) INFORMATION FOR SEQ ID NO:2:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:2:

```
Glu Val Gln Leu Gln Gln Ser Gly Thr Val Leu Ala Arg Pro Gly Ala
 1               5                  10                  15

Ser Val Lys Met Ser Cys Lys Ala Ser Gly Tyr Ser Phe Thr Arg Tyr
             20                  25                  30

Trp Met His Trp Ile Lys Gln Arg Pro Gly Gln Gly Leu Glu Trp Ile
         35                  40                  45

Gly Ala Ile Tyr Pro Gly Asn Ser Asp Thr Ser Tyr Asn Gln Lys Phe
     50                  55                  60

Glu Gly Lys Ala Lys Leu Thr Ala Val Thr Ser Ala Ser Thr Ala Tyr
 65                  70                  75                  80

Met Glu Leu Ser Ser Leu Thr His Glu Asp Ser Ala Val Tyr Tyr Cys
                 85                  90                  95

Ser Arg Asp Tyr Gly Tyr Tyr Phe Asp Phe Trp Gly Gln Gly Thr Thr
            100                 105                 110

Leu Thr Val Ser Ser
        115
```

(2) INFORMATION FOR SEQ ID NO:3:

(i) SEQUENCE CHARACTERISTICS:
        (A) LENGTH: 117 amino acids
        (B) TYPE: amino acid
        (D) TOPOLOGY: linear (ii) MOLECULE TYPE: protein

```
    (iii) HYPOTHETICAL: NO (iv) ANTI-SENSE: NO (ix) FEATURE:
         (A) NAME/KEY: Region
         (B) LOCATION: 1..30
         (D) OTHER INFORMATION: /label= FR1
             /note= "Framework Region 1"

(ix) FEATURE:
         (A) NAME/KEY: Binding-site
         (B) LOCATION: 31..35
         (D) OTHER INFORMATION: /label= CDR1
             /note= "Complementarity Determining Region 1"

(ix) FEATURE:
         (A) NAME/KEY: Region
         (B) LOCATION: 36..49
         (D) OTHER INFORMATION: /label= FR2
             /note= "Framework region 2"

(ix) FEATURE:
         (A) NAME/KEY: Binding-site
         (B) LOCATION: 50..66
         (D) OTHER INFORMATION: /label= CDR2
             /note= "Complementarity Determining Region 2"

(ix) FEATURE:
         (A) NAME/KEY: Region
         (B) LOCATION: 67..98
         (D) OTHER INFORMATION: /label= FR3
             /note= "Framework Region 3"

(ix) FEATURE:
         (A) NAME/KEY: Binding-site
         (B) LOCATION: 99..106
         (D) OTHER INFORMATION: /label= CDR3
             /note= "Complementarity Determining Region 3"

(ix) FEATURE:
         (A) NAME/KEY: Region
         (B) LOCATION: 107..117
         (D) OTHER INFORMATION: /label= FR4
             /note= "Framework Region 4"

(xi) SEQUENCE DESCRIPTION: SEQ ID NO:3:

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Arg Tyr
            20                  25                  30

Trp Met His Trp Ile Lys Gln Arg Pro Gly Gln Gly Leu Glu Trp Ile
        35                  40                  45

Gly Ala Ile Tyr Pro Gly Asn Ser Asp Thr Ser Tyr Asn Gln Lys Phe
50                  55                  60

Glu Gly Lys Ala Lys Leu Thr Ala Val Thr Ser Ala Ser Thr Ala Tyr
65                  70                  75                  80

Met Glu Leu Ser Ser Leu Thr His Glu Asp Ser Ala Val Tyr Tyr Cys
            85                  90                  95

Ser Arg Asp Tyr Gly Tyr Tyr Phe Asp Phe Trp Gly Gln Gly Thr Thr
            100                 105                 110

Leu Thr Val Ser Ser
        115

(2) INFORMATION FOR SEQ ID NO:4:

(i) SEQUENCE CHARACTERISTICS:
        (A) LENGTH: 555 base pairs
        (B) TYPE: nucleic acid
        (C) STRANDEDNESS: double
```

(D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 244..555

(ix) FEATURE:
        (A) NAME/KEY: sig_peptide
        (B) LOCATION: 1..243

(ix) FEATURE:
        (A) NAME/KEY: intron
        (B) LOCATION: 50..226

(ix) FEATURE:
        (A) NAME/KEY: misc_feature
        (B) LOCATION: 244..519
        (D) OTHER INFORMATION: /standard_name= "V Segment Gene"

(ix) FEATURE:
        (A) NAME/KEY: misc_feature
        (B) LOCATION: 520..555
        (D) OTHER INFORMATION: /standard_name= "J2 Segment Gene"

(xi) SEQUENCE DESCRIPTION: SEQ ID NO:4:

```
ATGGATTTTC AGGTGCAGAT TTTCAGCTTC CTGCTAATCA GTGCCTCAGG TAACAGAGGG      60

CAGGGAATTT GAGATCAGAA TCCAACCAAA ATTATTTTCC CTGGGGAATT TGAGTCTAAA     120

ATACAGTTTT TTTTTCTTTT TCTTCATCTG AATGTTGGGT GGTATAAAAT TATTTTTGTT     180

TCTCTATTTC TACTAATCCC TTTCTCTCTA TTTTGCTTTT TTCTAGTCAT ACTGTCCAGA     240
```

```
GGA CAA ATT GTT CTC ACC CAG TCT CCA GCA ATC ATG TCT GCA TCT CCA      288
    Gln Ile Val Leu Thr Gln Ser Pro Ala Ile Met Ser Ala Ser Pro
      1               5                  10                 15

GGG GAG AAG GTC ACC ATG ACC TGC AGT GCC AGC TCA AGT ATA AGT TAC      336
Gly Glu Lys Val Thr Met Thr Cys Ser Ala Ser Ser Ser Ile Ser Tyr
              20                  25                  30

ATG CAG TGG TAC CAG CAG AAG CCA GGC ACC TCC CCC AAA AGA TGG ATT      384
Met Gln Trp Tyr Gln Gln Lys Pro Gly Thr Ser Pro Lys Arg Trp Ile
          35                  40                  45

TAT GAC ACA TCC AAA CTG GCT TCT GGA GTC CCT GCT CGC TTC AGT GGC      432
Tyr Asp Thr Ser Lys Leu Ala Ser Gly Val Pro Ala Arg Phe Ser Gly
      50                  55                  60

AGT GGG TCT GGG ACC TCT TAT TCT CTC ACA ATC AGC AGC ATG GAG GCT      480
Ser Gly Ser Gly Thr Ser Tyr Ser Leu Thr Ile Ser Ser Met Glu Ala
  65                  70                  75

GAA GAT GCT GCC ACT TAT TAC TGC CAT CAG CGG AGT AGT TAC ACG TTC      528
Glu Asp Ala Ala Thr Tyr Tyr Cys His Gln Arg Ser Ser Tyr Thr Phe
80                  85                  90                  95

GGA GGG GGG ACC AAA CTG GAA ATA AAA                                   555
Gly Gly Gly Thr Lys Leu Glu Ile Lys
                100
```

(2) INFORMATION FOR SEQ ID NO:5:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:5:

```
Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Ile Ser Tyr Met
            20                  25                  30

Gln Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys
            100
```

(2) INFORMATION FOR SEQ ID NO:6:

(i) SEQUENCE CHARACTERISTICS:
        (A) LENGTH: 104 amino acids
        (B) TYPE: amino acid
        (D) TOPOLOGY: linear (ii) MOLECULE TYPE: protein (iii) HYPOTHETICAL: NO (iv) ANTI-SENSE: NO (ix) FEATURE:
        (A) NAME/KEY: Region
        (B) LOCATION: 1..23
        (D) OTHER INFORMATION: /label= FR1'
           /note= "Framework Region 1'"

(ix) FEATURE:
        (A) NAME/KEY: Binding-site
        (B) LOCATION: 24..33
        (D) OTHER INFORMATION: /label= CDR1'
           /note= "Complementarity Determining Region 1'"

(ix) FEATURE:
        (A) NAME/KEY: Region
        (B) LOCATION: 34..48
        (D) OTHER INFORMATION: /label= FR2'
           /note= "Framework Region 2'"

(ix) FEATURE:
        (A) NAME/KEY: Binding-site
        (B) LOCATION: 49..55
        (D) OTHER INFORMATION: /label= CDR2'
           /note= "Complementarity Determining Region 2'"

(ix) FEATURE:
        (A) NAME/KEY: Region
        (B) LOCATION: 56..87
        (D) OTHER INFORMATION: /label= FR3'
           /note= "Framework Region 3'"

(ix) FEATURE:
        (A) NAME/KEY: Binding-site
        (B) LOCATION: 88..94
        (D) OTHER INFORMATION: /label= CDR3'
           /note= "Complementarity Determining Region 3'"

(ix) FEATURE:
        (A) NAME/KEY: Region
        (B) LOCATION: 95..104
        (D) OTHER INFORMATION: /label= FR4'
           /note= "Framework Region 4'"

(xi) SEQUENCE DESCRIPTION: SEQ ID NO:6:

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
                20                  25                  30

Gln Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys
            100
```

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:7:

```
Arg Tyr Trp Met His
1               5
```

(2) INFORMATION FOR SEQ ID NO:8:

(i) SEQUENCE CHARACTERISTICS:
        (A) LENGTH: 17 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:8:

```
Ala Ile Tyr Pro Gly Asn Ser Asp Thr Ser Tyr Asn Gln Lys Phe Glu
1               5                   10                  15
Gly
```

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:9:

Asp Tyr Gly Tyr Tyr Phe Asp Phe
1               5

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:10:

Ser Ala Ser Ser Ser Ile Ser Tyr Met Gln
1               5                   10

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:11:

Asp Thr Ser Lys Leu Ala Ser
1               5

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:12:

His Gln Arg Ser Ser Tyr Thr
1               5